(12) United States Patent
Knox et al.

(10) Patent No.: US 11,690,759 B2
(45) Date of Patent: *Jul. 4, 2023

(54) METHOD FOR MODIFYING THE REFRACTIVE INDEX OF OCULAR TISSUES AND APPLICATIONS THEREOF

(71) Applicant: University of Rochester, Rochester, NY (US)

(72) Inventors: Wayne H. Knox, Rochester, NY (US); Krystel R. Huxlin, Rush, NY (US)

(73) Assignee: University of Rochester, Rochester, NY (US)

( * ) Notice: Subject to any disclaimer, the term of this patent is extended or adjusted under 35 U.S.C. 154(b) by 275 days.

This patent is subject to a terminal disclaimer.

(21) Appl. No.: 17/072,286

(22) Filed: Oct. 16, 2020

(65) Prior Publication Data
US 2021/0045920 A1 Feb. 18, 2021

Related U.S. Application Data

(63) Continuation of application No. 13/326,403, filed on Dec. 15, 2011, now Pat. No. 10,813,791.
(Continued)

(51) Int. Cl.
*A61F 9/008* (2006.01)

(52) U.S. Cl.
CPC ...... *A61F 9/00827* (2013.01); *A61F 9/00834* (2013.01); *A61F 2009/0087* (2013.01);
(Continued)

(58) Field of Classification Search
CPC ........ A61F 2009/00842; A61F 9/00834; A61F 9/00827
See application file for complete search history.

(56) References Cited

U.S. PATENT DOCUMENTS

| 3,948,248 A | 4/1976 | Zuckerman et al. |
| 5,777,719 A | 7/1998 | Williams et al. |

(Continued)

FOREIGN PATENT DOCUMENTS

| JP | 39-178901 A | 7/1997 |
| JP | 2001-147301 A | 5/2001 |

OTHER PUBLICATIONS

Denk et al. (1990) "Two-Photon Laser Scanning Fluorescence Microscopy," Science 248(4951):73-76.
(Continued)

*Primary Examiner* — Lynsey C Eiseman
*Assistant Examiner* — Amanda L Steinberg
(74) *Attorney, Agent, or Firm* — Andrew J. Anderson, Esq.; Harter Secrest & Emery LLP

(57) ABSTRACT

A method for modifying a refractive property of ocular tissue in an eye by creating at least one optically-modified gradient index (GRIN) layer in the corneal stroma and/or the crystalline by continuously scanning a continuous stream of laser pulses having a focal volume from a laser having a known average power along a continuous line having a smoothly changing refractive index within the tissue, and varying either or both of the scan speed and the laser average power during the scan. The method may further involve determining a desired vision correction adjustment, and determining a position, number, and design parameters of gradient index (GRIN) layers to be created within the ocular tissue to provide the desired vision correction.

20 Claims, 25 Drawing Sheets

Related U.S. Application Data

(60) Provisional application No. 61/492,559, filed on Jun. 2, 2011, provisional application No. 61/492,586, filed on Jun. 2, 2011.

(52) U.S. Cl.
CPC .......... *A61F 2009/0088* (2013.01); *A61F 2009/00842* (2013.01); *A61F 2009/00846* (2013.01); *A61F 2009/00872* (2013.01)

(56) References Cited

U.S. PATENT DOCUMENTS

| | | |
|---|---|---|
| 5,849,006 A | 12/1998 | Frey et al. |
| 6,261,220 B1 | 7/2001 | Frey et al. |
| 6,270,221 B1 | 8/2001 | Liang et al. |
| 6,271,914 B1 | 8/2001 | Frey et al. |
| 6,478,792 B1 | 11/2002 | Hansel |
| 7,789,910 B2 | 9/2010 | Knox et al. |
| 8,292,952 B2 | 10/2012 | Bille |
| 8,486,055 B2 | 7/2013 | Knox et al. |
| 8,617,147 B2 | 12/2013 | Knox et al. |
| 9,078,732 B2 † | 7/2015 | Dick |
| 9,144,491 B2 | 9/2015 | Knox et al. |
| 9,492,323 B2 | 11/2016 | Knox et al. |
| 10,813,791 B2 | 10/2020 | Knox et al. |
| 2008/0001320 A1 | 1/2008 | Knox et al. |
| 2009/0005764 A1* | 1/2009 | Knox .............. A61F 9/008 606/5 |
| 2009/0287306 A1 | 11/2009 | Smith et al. |
| 2010/0210996 A1* | 8/2010 | Peyman ............ A61F 9/0079 604/20 |
| 2010/0228345 A1 | 9/2010 | Bille |
| 2010/0249761 A1 | 9/2010 | Ruiz et al. |
| 2011/0071509 A1 | 3/2011 | Knox et al. |
| 2015/0378065 A1 | 12/2015 | Knox et al. |

OTHER PUBLICATIONS

Ding et al. (2006) "Large refractive index change in silicone-based and non-silicone-based hydrogel polymers induced by femtosecond laser micro-machining," Optics Express 14(24): 11901-11909.

Ding et al. (2008) "Intratissue Refractive Index Shaping of the Cornea and Lens Using a Low Pulse Energy Femtosecond Laser Oscillator," Investigative Ophthalmology & Visual Science 49(12): 5332-5339.

Eaton et al. (2005) "Heat accumulation effects in femtosecond laser-written waveguides with variable repetition rate," Optics Express 13(12): 4708-4716.

Giguere et al. (2007) "Laser ablation threshold dependence on pulse duration for fused silica and corneal tissues: experiments and modeling," Journal of the Optical Society of America A 24(6): 1562-1568.

Juhasz et al. (1999) "Corneal refractive surgery with femtosecond lasers," IEEE Journal of Quantum Electronics 5(4): 902-909.

Konig et al. (2002) "Intratissue surgery with 80MHz nanojoule femtosecond laser pulses in the near infrared," Optics Express 10(3): 171-176.

Kuriz et al. (1998) "Lamellar refractive surgery with scanned intrastromal picosecond and femtosecond laser pulses in animal eyes," Journal of Refractive Surgery 14(5):541-548.

Loesel et al. (1996) "Laser-induced optical breakdown on hard and soft tissue and its dependence on the pulse duration: experiment and model," IEEE Journal of Quantum Electronics 32(10): 1717-1722.

NAGY et al. (Feb. 2010) "Potentiation of Femtosecond Laser Intratissue Refractive Index Shaping," Investigative Ophthalmology & Visual Science 51(2): 850-856.

Vogel et al. (2005) "Mechanisms of femtosecond laser nanosurgery of cells and tissues," Applied Physics B 81: 1015-1047.

Watanabe et al. Fabrication of fresnel zone plate embedded in silica glass by femtosecond laser pulses Sep. 23, 2002; Optics Express 10(19): 978-983.

Xu et al. (Oct. 2010) "Non-invasive Blue Intra-tissue Refractive Index Shaping -IRIS- In Living Excised Cornea," Frontiers in Optics 2010, Rochester, New York United States: 24-28.

Xu et al. (Oct. 2011) "Noninvasive Intratissue Refractive Index Shaping (IRIS) of the Cornea with Blue Femtosecond Laser Light," Investigative Ophthalmology & Visual Science 52(11): 8148-8155.

Xu et al. (Nov. 2011) "Lateral gradient index microlenses written in ophthalmic hydrogel polymers by femtosecond laser micromachining," Optical Materials Express 1(8): 1416-1424.

Xu et al. (2011) "Exogenous and Endogenous Two-Photon Absorption for Intratissue Refractive Index Shaping (IRIS) in Corneal Tissue," Nonlinear Optics: OSA Technical Digest, paper NTuF1.

\* cited by examiner
† cited by third party

METHOD FOR MODIFYING THE REFRACTIVE INDEX OF OCULAR TISSUES AND APPLICATIONS THEREOF

RELATED APPLICATION DATA

This application is a continuation of application Ser. No. 13/326,403 filed Dec. 15, 2011, which claims the benefit under 35 USC 119(e) of Provisional Patent Application Nos. 61/492,559 and 61/492,586, both filed Jun. 2, 2011, the subject matters of which are incorporated by reference herein in their entireties.

CREATE ACT STATEMENT

The claimed invention was made by, on behalf of, or in connection with one or more of the following parties to a joint university-corporation research agreement: The University of Rochester and Bausch & Lomb, Inc. The agreement was in effect on and before the date the claimed invention was made, and the claimed invention was made as a result of activities undertaken within the scope of the agreement.

BACKGROUND

Field of the Invention

Embodiments of the invention are directed to a method for using a laser to modify the refractive index of ocular tissues, e.g., the corneal stroma or lens cortex, for vision correction, and applications thereof for correcting and/or optimizing vision.

Description of Related Art

Conventional ultraviolet nanosecond excimer lasers have been very successfully used for corneal refractive surgery such as photorefractive keratectomy (PRK), laser-assisted in-situ keratomileusis (LASIK) and laser sub-epithelial keratomileusis (LASEK). By ablating corneal tissue through direct, one-photon absorption of ultraviolet light, these lasers are able to alter the curvature and thickness of corneas, ultimately altering their optical power.

The rapid development of femtosecond laser technology has provided an additional tool for corneal refractive surgery. In contrast to the photo-ablative ultraviolet lasers, femtosecond laser pulses in the near infrared or visible range can pass through transparent corneal tissue without significant one-photon absorption. Only when pulses are focused inside the cornea, is the intensity of the beam sufficient to cause nonlinear, typically, multi-photon absorption. Because the absorption is nonlinear, the laser-affected region tends to be highly localized, leaving the surrounding region unaffected, or minimally affected. See, Vogel A, Noack J, Huttman G, Paltauf G, Mechanisms of femtosecond laser nano-surgery of cells and tissues. *Applied Physics B* 2005, 81, 1015-47; Loesel F H, Niemz M H, Bille J F, Juhasz T, Laser-induced optical breakdown on hard and soft tissue and its dependence on the pulse duration: experiment and model. *IEEE Journal of Quantum Electronics* 1996, 32, 1717-22; and Giguere D, Olivie G, Vidal F, et al., Laser ablation threshold dependence on pulse duration for fused silica and corneal tissues: experiments and modeling, *Journal of the Optical Society of America A* 2007, 24, 1562-68. Also, several studies on the effects of high-repetition-rate femtosecond lasers on fused silica and borosilicate glass have found that laser pulses greatly increased the temperature of the materials at the laser focus. See, Eaton et al, *Optics Express* 2005, 13, 4708-16. Vogel calculated the temperature change in water would be >10° K with a 0.6 NA focusing lens and 100 fs laser pulses assuming that with each pulse, an energy density of 1 $J/cm^3$ at the center of the initial temperature distribution is deposited.

In the past two decades, extensive experimental and theoretical work has been done to characterize laser-induced optical breakdown thresholds in different materials, including the cornea and the natural crystalline lens. Most of this work, however, centered on the use of continuous wave (CW) lasers or on single pulses from low repetition rate lasers in which thermal diffusion time is much shorter than the time interval between adjacent pulses. Thus, each pulse is responsible for a change in the material. Indeed, it has been established that for pulses longer than 10 ps, the optical breakdown threshold fluence scales as the square root of the pulse duration. To date, most femtosecond lasers used to cut corneas in clinical practice use microJoule (µJ) femtosecond laser pulses with a low-repetition-rate (Hz-kHz range) and spot diameters of more than 5 microns (µm). See, Kurtz R M, Horvath C, Liu H H, Krueger R R, Juhasz T, Lamellar refractive surgery with scanned intrastromal picosecond and femtosecond laser pulses in animal eyes, *Journal of Refractive Surgery* 1998, 14, 541-48; and Juhasz T, Loesel C, Horvath C, Kurtz R M, Mourou G, Corneal refractive surgery with femtosecond lasers, *IEEE Journal of Quantum Electronics* 1999, 5, 902-09.

This contrasts with the range of femtosecond laser parameters that have been established for biomedical applications. See, Loesel F H, Niemz M H, Bille J F, Juhasz T, Laser-induced optical breakdown on hard and soft tissue and its dependence on the pulse duration: experiment and model, *IEEE Journal of Quantum Electronics* 1996, 32, 1717-22. Compared with the low-repetition-rate femtosecond lasers with µJ or milliJoule (mJ) pulse energies, high-repetition-rate (>1 MHz) femtosecond laser oscillators usually have pulse energies on the order of nanoJoules (nJ). Such low-pulse-energy femtosecond lasers have been used for both micromachining and nanosurgery. See, König K, Krauss O, Riemann I, Intratissue surgery with 80 MHz nanojoule femtosecond laser pulses in the near infrared, *Optics Express* 2002, 10, 171-76.

U.S. Pat. No. to Hansel generically describes a method and a device for irradiation of ocular tissues that can be used for such applications as refractive surgery and laser medicine. The method described is said to combine the "working principles of specific optical and electronic modules to expose the eye lens to controlled therapeutic radiation in the long-wave UV-A range above cornea absorption and/or the visible and/or the near infra-red ranges and/or the cornea in a defined way to treatment radiation in the near infra-red wavelength range about 1.3 micrometers" (see, Hansel Abstract). The therapeutic radiation is also said to provide "locally photo-induced irreversible chemical changes are created in the eye lens substance and/or the cornea substance such that the refractive index and/or the transmission properties for visible useful radiation can be changed to predefined parameters, resulting in a defect-reduced vision." Id.

U.S. publication No. 2010/0228345 discloses a system for forming and modifying lenses and lenses formed thereby. The disclosed method uses bursts of femtosecond (fs) laser pulses to create loci, which act to alter the optical phase of light passing there through. However, the resulting modified regions in the material are up to 50 microns (µm) thick to achieve the desired dioptric changes. The publication further discloses that the method can be applied to ocular tissue.

There exists an ongoing need for ways to improve or correct vision. Changing the refractive index of ocular tissue, e.g., the corneal stroma or lens cortex, using a femtosecond laser, without tissue destruction or wound healing response would be advantageous. The inventors have recognized that it would be especially advantageous to improve or correct vision by changing the refractive property of the corneal stroma and/or crystalline, which could potentially eliminate the need for vision aids such as, e.g., glasses, contact lenses, and/or ophthalmic laser surgery (e.g., LASIK, LASEK, etc.).

SUMMARY

An embodiment of the invention is directed to a method for forming a refractive structure in a living eye. The method includes the steps of directing and focusing a plurality of femtosecond laser pulses in a spectral region between about 350 nanometers (nm) to about 600 nm within a cornea or a lens of the living eye; controlling the intensity of the laser pulses to have an intensity sufficient to change the refractive index of the cornea or lens within a defined focal region, but below a damage threshold the cornea or lens, or at a level that will not photo-disrupt cornea or lens tissue outside of the focal region; and forming a refractive structure in the focal region of the cornea or the lens by scanning the laser pulses through a volume of the cornea or the lens. Each refractive structure is characterized by a change in refractive index, and exhibits little or no scattering loss.

An embodiment of the invention is directed to a method for providing vision correction to a patient. The method includes: (a) measuring the degree of vision correction needed by the patient and determining the location and shape of a refractive structure that needs to be positioned within the cornea to partially correct a patient's vision; (b) directing and focusing femtosecond laser pulses in the blue spectral region within the cornea at an intensity high enough to change the refractive index of the cornea within a focal region, but not high enough to damage the cornea or to affect cornea tissue outside of the focal region; and (c) scanning the laser pulses across a volume of the cornea or the lens to provide the focal region with a refractive structure in the cornea or the lens. Again, the refractive structure is characterized by a change in refractive index, and exhibits little or no scattering loss.

An embodiment of the invention is directed to a method for forming a refractive structure in a living eye, comprising: directing and focusing a plurality of femtosecond laser pulses in a spectral region between about 350 nanometers (nm) to about 600 nm within a defined focal region in the cornea or lens of the living eye, wherein the laser pulses have a repetition rate from 10 MHz to 300 MHz, a pulse duration of 30 fs to 200 fs, an average power from 20 mW to 160 mW, and a pulse energy from 0.01 nJ to 10 nJ; further wherein the defined focal region is in the form of a cylindrical volume having a diameter between about 1.0 µm to 2 µm and a length between about 3 µm to 6 µm; and forming a refractive structure in the focal region of the cornea or the lens, further comprising creating a difference in the refractive index of the refractive structure from that outside of the focal region by between about 0.005 to 0.06 without photo-disrupting cornea or lens tissue outside of the focal region. According to an aspect, the spectral region is between about 375 nm to about 425 nm. According to an aspect, the spectral region is between about 350 nm to about 400 nm. According to an aspect, the laser pulses have a wavelength of about 400 nm. According to an aspect, the pulse energy is between about 0.1 nJ to 2 nJ. According to an aspect, the method further comprises forming the refractive structure having a structural form of at least one of a lens, a prism, a Bragg grating, a microlens arrays, a zone plate, a Fresnel lenses, and a combination thereof.

An embodiment of the invention is a method for modifying a refractive property of ocular tissue in an eye. The method includes the steps of creating at least one optically-modified gradient index (GRIN) layer in either the corneal stroma or the crystalline lens (or both) having a gradient index of refraction in either one or two directions that are generally transverse to the direction of light propagation through the tissue by continuously scanning a continuous stream of laser pulses having a focal volume from a laser having a known average power along a continuous line having a smoothly changing refractive index within the tissue, and varying either the scan speed or the laser average power or both during the scan. According to various non-limiting aspects and illustrative embodiments,

- the method further comprising continuously scanning a continuous stream of laser pulses having a focal volume from a laser having a known average power along a continuous line of constant depth;
- the method further comprising creating the at least one GRIN layer having a constant GRIN layer thickness d between about one to 10 µm;
- the method further comprising forming a gradient index of refraction in the GRIN layer in two orthogonal directions;
- the method further comprising creating a plurality of laser scan lines in an adjacent, spaced relationship in the ocular tissue;
- the method further comprising creating a plurality of straight scan lines;
- the method further comprising creating a plurality of straight scan lines wherein each of the lines has a width of between about one to five µm and an interline spacing that is equal to or less than the line width;
- the method further comprising creating a plurality of straight scan lines, wherein each of the lines has a width of between about one to five µm and an interline spacing that is equal to or less than the line width, wherein the spacing is equal to or less than one µm;
- the method further comprising creating between about 2,500 to 20,000 lines in the GRIN layer;
- the method wherein the GRIN layer is a planar layer;
- the method further comprising creating at least two optically-modified GRIN layers having an interlayer spacing, S, equal to or greater than five µm;
- the method further comprising determining the scan speed as a function of the selected gradient index of refraction along the scan line;
- the method further comprising scanning with a laser beam having a wavelength in the range from 650 nm to 1000 nm, an average laser power from 50 mW to 1000 mW, a pulse width of between five fs to 200 fs, a pulse repetition rate of between 10 MHz to 500 MHz, and a pulse energy between 0.01 nJ and 100 nJ;
- the method further comprising creating a quadratic or a non-quadratic gradient index profile in the GRIN layer;
- the method further comprising creating a quadratic gradient index of refraction of one given magnitude and orientation in at least one GRIN layer and a quadratic gradient index of refraction of a different given magnitude and orientation in a different GRIN layer;

the method further comprising creating a cylindrical focusing power in the ocular tissue;

the method wherein the step of varying the scan speed and/or the laser power further comprises varying the scan speed between equal to or greater than one mm/sec;

the method further comprising determining a desired vision correction adjustment, and determining a position, number, and design parameters of gradient index (GRIN) layers to be created within the ocular tissue to provide the desired vision correction.

Related embodiments of the invention are a method and apparatus for controlling and monitoring short light pulses from a laser to form a scan line(s) that can be written into eye tissue at a depth of up to five mm or more. High (nearly diffraction-limited) focus is maintained by an adaptive optic element with real-time feedback during scanning operations using an active feedback that is provided by a two-photon fluorescence signal. The method enables real-time feedback and a real-time compensation technique that provides instantaneous information regarding the quality of the focused beam, which must be maintained at near-diffraction-limited performance throughout the scanning operation. According to an aspect, we use an epi-mode (back-detected), exogenous or endogenous (from a two-photon chromophore that is used as a two-photon enhancer in the IOL or ocular tissue) two-photon fluorescence signal as a detector of the focus quality.

BRIEF DESCRIPTION OF THE DRAWINGS

The embodied invention will be better understood from the following description and in consideration with the accompanying figures. It is to be expressly understood, however, that each of the figures is provided to further illustrate and describe the invention and is not intended to further limit the invention claimed.

DETAILED DESCRIPTION OF EMBODIMENTS OF THE INVENTION

Figure 1:
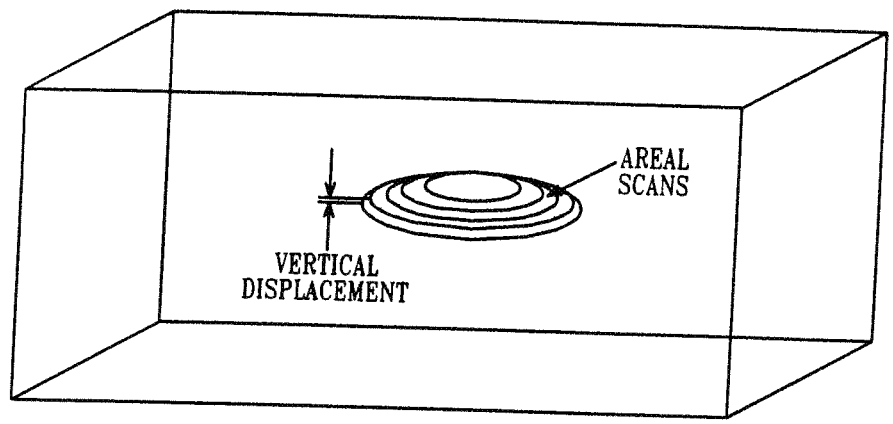
FIG. 1 is a schematic representation of a three-dimensional structure in the cornea stroma that can be produced by the method described.

Using very high-repetition-rate, ultra-short laser pulses we determined that the optical breakdown threshold for a 0.70 NA focusing condition in lightly-fixed cornea stroma and lens cortex is from about 40 mW to 90 mW average laser power, respectively. For both cornea stroma and lens cortex both values are lower than the optical breakdown power reported by Konig and colleagues using 1 nJ pulse energy, 170 fs pulse duration and 1.30 NA focusing in porcine corneas. See, Konig et al, Optics Express 2002, 10(3), 171-76. By using 30 mW and 45 mW average laser power (0.3 nJ and 0.5 nJ pulses), we discovered that one can induce Intra-tissue Refractive Index Shaping (IRIS), without accompanying photo-disruption and tissue destruction.

We adapted our femtosecond micromachining approach with hydrogel materials to carry out IRIS in biological tissues. We initially measured the optical breakdown thresholds of lightly-fixed cat corneas and lenses. We then reduced femtosecond laser pulse energies below these optical breakdown thresholds to create grating patterns that are associated with a change in the refractive index of the tissue. Our investigation has led to the development of a process to modify the refractive index of ocular tissue, e.g., corneal stroma and lens cortex, without apparent tissue destruction. Accordingly, a determination of the appropriate laser parameters is important for achieving IRIS in biological tissues. Not only does the femtosecond laser fluence at the objective focus have to be below the optical breakdown threshold of the tissue, the laser fluence must be strong enough to induce nonlinear changes in the tissues. Moreover, the scan speed must be set within a specified range.

The process involves irradiating the ocular tissue with a high repetition, low-pulse-energy, femtosecond laser. If very short laser pulses having a very select energy are focused on ocular tissue, the total intensity of light leads to a change in the refractive index of the ocular tissue in the focal region. Moreover, the region of the ocular tissue just outside the focal region is minimally affected by the laser light. As a result, select volumes of ocular tissue can be modified resulting in a change in the refractive index in these tissue volumes. Moreover, the long-term stability of the observed change in refractive index suggests permanent molecular and/or structural changes to the ocular tissue An embodiment of the invention is directed to a method for forming refractive structures in a living eye. The method includes (a) directing and focusing femtosecond laser pulses in the blue spectral region within a cornea or a lens of the living eye at an intensity high enough to change the refractive index of the cornea or lens within a focal region, but not high enough to damage the cornea or lens or to affect cornea or lens tissue outside of the focal region; and (b) scanning the laser pulses across a volume of the cornea or the lens to provide the focal region with refractive structures in the cornea or the lens. The refractive structures exhibit little or no scattering loss, which means that the structures are not clearly visible under appropriate magnification without contrast enhancement.

In one embodiment, the method can further include measuring the degree of vision correction needed by a patient following cataract surgery prior to step (a), and determining the location and shape of the refractive structures that need to be positioned within the cornea to correct the patient's vision. In another embodiment, the method can further include measuring the degree of vision correction needed by a patient prior to step (a), and determining the location and shape of the refractive structures that need to be positioned within the cornea to correct the patient's vision.

In another embodiment, the determined change in refractive index induced in cornea and lens tissue using the described process is relatively small, but very significant. Based on published values for the power (39D) and native refractive index (1.376) of the cat cornea, IRIS should generate a change in corneal power ranging between 0.14D and 0.56D (assuming an index change between 0.005 and 0.02). Similarly, for the cat lens (power=53D, refractive index of the homogeneous lens=1.554), the refractive index changes induced by micromachining should theoretically alter lenticular power by between 0.5D and 0.7D. The laser process described could completely alter the approach to laser refractive surgery and to vision correction.

In addition, the preservation of tissue clarity during the treatment allows the application of IRIS for the creation of corneal fiducial markings that could be used to align eye trackers during LASIK, and for refractive corrections in a closed-loop approach, e.g. with specific benefit for the correction of higher-order aberrations, as well as for "touch-up corrections" of ocular surface defects. Various types of refractive structures can be created in biological tissues. Examples include high refractive index structures such as Bragg gratings, microlens arrays, optical zone plates, and Fresnel lenses.

As stated, the determination and selection of the laser operating parameters are particularly important in implementing IRIS. The inventors have found that various ranges of parameters are particularly useful in implementing the present invention. In treatment of the eye, the laser wavelength should be such that the tissues through which laser pulses pass are transparent to the pulses. There should also be no damage to the retina; any change should be confined to the tissue within the focal region. Also, for non-destructive alteration of ocular tissue, a $CO_2$ laser or excimer laser should not be used, since there should be no ablation or removal of the tissue.

A laser pulse frequency from 1 MHz to 10 GHz, and preferably from 10 to 300 MHz, should be used. For example, our work used a laser pulse frequency (repetition rate) of 70 MHz to 100 MHz, e.g., about 93 MHz or about 80 MHz.

Linked to the pulse frequency is a pulse duration of about 30 fs to about 200 fs. For example, a laser pulse duration of 80 fs to 120 fs.

Linked to the pulse frequency is the average laser power. A preferable average laser power is from 1 mW to 1,000 mW, e.g., from 20 mW to 160 mW, and more preferably from 60 mW to 110 mW.

The energy of each pulse should be in a range from 0.01 nJ to 10 nJ, preferably from 0.1 nJ to 2 nJ, and more preferably less than 1 nJ. For example, we have determined that a pulse energy from 0.1 nJ to 0.5 nJ, is a preferred energy range.

The laser pulse will have a peak intensity at focus of greater than $10^{13}$ W/$cm^2$. At times, it may be advantageous to provide a laser with a peak intensity at focus of greater than $10^{14}$ W/$cm^2$, or greater than $10^{15}$ W/$cm^2$.

We found that by using femtosecond laser pulses in the blue spectral region one can achieve high native nonlinear absorption so that the observed changes in index of refraction are strongly localized in three dimensions. The wavelength is chosen such that there is minimal visual sensitivity, high retinal damage threshold, and no UV photophysical one-photon damage mechanisms induced in the eye. And furthermore, the technique is performed in such a manner that there is minimal death to the live cells in the stroma, which can reduce the wound healing response from the procedure.

Linked to one or more of the above laser pulse parameters is the speed (mm/s) at which the laser pulses is scanned across a volume of the ocular tissue. Although scanning speeds as low as 0.05 mm/s can be used depending on the equipment, types of structures to be written and type of ocular tissue, greater scan speeds in a range from 0.1 mm/s to 30 mm/s are generally preferred. We have generally utilized scan speeds of 1 mm/s to 15 mm/s, e.g., 1 mm/s, 5 mm/s, 10 mm/s and 15 mm/s keeping all other laser parameters constant (wavelength 400 nm; average laser power 80 mW, pulse duration 100 fs to form refractive structures 150 µm into the corneal stroma.

The refractive structures are formed by scanning the laser pulses across a volume of ocular tissue. The affected regions wherein the index of refraction is changed are cylindrical volumes from about 0.5 µm to 3 µm in diameter and 3 µm to 10 µm in length. By scanning the laser pulses across the tissue the cylindrical volumes form continuous refractive structures in two or three dimensions. In one embodiment, the focal region can be defined by a cylindrical volume from about 1.0 µm to 2 µm in diameter and 3 µm to 6 µm in length.

The pulse energy of the focused laser used in the method will in-part depend on the type of structures to be written into the ocular tissue, the type of ocular tissue and how much of a change in refractive index is desired. The selected pulse energy will also depend upon the scan rate at which the structures are written into the ocular tissue. Typically, greater pulse energies will be needed for greater scan rates.

The pulse width must be preserved so that the pulse peak power is strong enough to exceed the nonlinear absorption threshold of the ocular tissue. However, the glass of the focusing objective(s) significantly increases the pulse width due to the positive dispersion of the glass. A compensation scheme is used to provide a corresponding negative dispersion that can compensate for the positive dispersion introduced by the focusing objective(s). Accordingly, the term "focused" in this application refers to the focusing of light from a laser within ocular tissue using a compensation scheme to correct for the positive dispersion introduced by the focusing objective(s). The compensation scheme can include an optical arrangement selected from the group consisting of at least two prisms and at least one mirror, at least two diffraction gratings, a chirped mirror, and dispersion compensating mirrors to compensate for the positive dispersion introduced by the focus objective.

In one embodiment, the compensation scheme comprises at least one prism, in many cases at least two prisms, and at least one mirror to compensate for the positive dispersion of the focusing objective. In another embodiment, the compensation scheme comprises at least two gratings to compensate for the positive dispersion of the focusing objective. Any combination of prisms, gratings and/or mirrors can be used for the compensation scheme in accordance with optical principles known by those of ordinary skill in the art.

As stated, the refractive structures can be defined by two- or three-dimensional structures. The two- or three-dimensional structures can comprise an array of discrete cylinders. Alternatively, the two- or three-dimensional structures can comprise a series of lines (a grating) or a combination of an array of cylinders and a series of lines. Moreover, the two- or three-dimensional structures can comprise area or volume filled structures, respectively. These area or volume filled structures are formed by continuously scanning the laser over a select plane or volume of the ocular tissue, respectively. As stated, various types of refractive structures can be created in biological tissues. Examples include high refractive index structures such as lenses, prisms, Bragg gratings, microlens arrays, optical zone plates, and Fresnel lenses.

Figure 2:
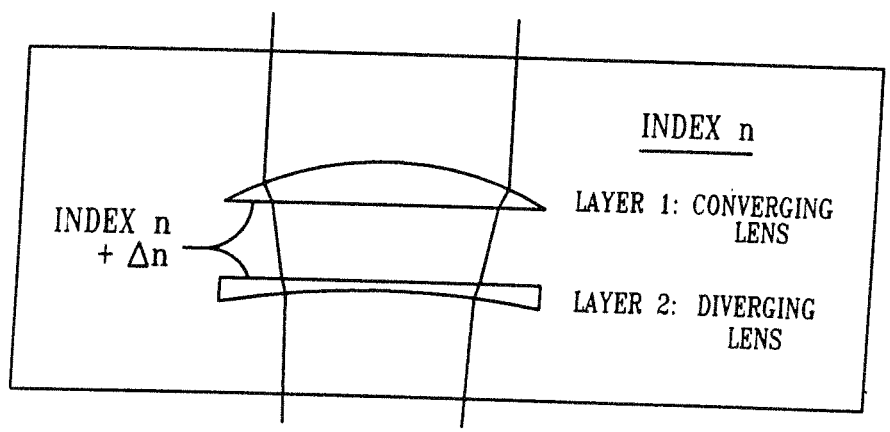
FIG. 2 is a schematic representation of creating a convex, plano or concave structure in cornea stroma to yield a positive or negative vision correction by the method described.

The area-filled or volume-filled two- or three-dimensional structures can be formed by continuously scanning the laser over select volumes of the ocular tissue. Refractive-type optical devices can be micro-machined inside the volume of ocular tissue by repeatedly scanning a tightly focused beam of femtosecond pulses in an area segment. The area of the segment can be changed correspondingly with the depth of the scan, so as to produce three-dimensionally shaped lenses with spheric, aspheric, toroidal or cylindrical shapes as shown in FIG. 1. Alternatively, refractive corrective lenses can be made in various combinations of convex, plano- or concave to yield a positive correction, or negative correction, as shown in FIG. 2. The refractive optical devices can be stacked vertically, written separately in different planes, so as to act as a single lens. Additional corrective layers can be written as desired.

In one embodiment, the focal region of the ocular tissue is defined by a series of lines in an approximately two dimensional plane having a width from 0.2 µm to 3 µm, preferably a width from 0.6 µm to 1.5 µm and a height from 0.4 µm to 8 µm, preferably a height from 1.0 µm to 4 µm (height is measured in the z direction, which is parallel to direction of the laser light). For example, one can generate a line array comprising a plurality of lines with each line of any desired length, about 0.8 µm to about 5 µm, about 0.8 µm to about 3 µm or about 0.8 µm to about 1.5 µm in width and about 2 µm to about 10 µm about 2 µm to 5 µm in height. The lines can be separated by as little as 1.0 µm (0.5 µm spacing), and any number of lines can be incorporated into the ocular tissue. Moreover, the line array can be positioned at any selected depth (z-direction), and any number of line arrays can be generated at various depths into the ocular tissue.

In one embodiment, the refractive structures placed in corneal stroma will exhibit a change in the index of refraction of about 0.005 to about 0.06, and typically about 0.01 to 0.04. This observed change in the index of refraction is relative to the bulk cornea stroma outside the focal region. Based on published values for the power (39D) and native refractive index (1.376) of the cat cornea, the refractive index changes induced by micromachining should generate a change in corneal power ranging between 0.1D and 01.0D or 0.1D and 0.5D (assuming that refractive index change affects the thickness of the cornea uniformly).

Our initial work with 800 nm light demonstrated that it is possible to cause low-scattering-loss, refractive index modifications in lightly-fixed cat cornea and lens using 93 MHz repetition rate, 27 fs laser pulses with 0.3 nJ and 0.5 nJ pulse energies. The use of near-infrared light that is just beyond the visual response on the long wavelength end is desirable for use in live eyes, since it would provide minimal retinal stimulation and eye aversion response. These modifications were visible only using DIC microscopy and were not associated with apparent tissue damage. The resulting modifications correspond to refractive index changes between 0.05±0.001 and 0.021±0.001. Preservation of IRIS over a month of refrigerated storage suggested that the femtosecond laser-induced modifications were likely to involve relatively long-term molecular/structural alterations. In related experiments involving silicone hydrogels, the micromachined gratings (and associated Raman spectra) are stable for at least one year, even after drying and rehydration of the hydrogel.

For example, it is possible to cause low-scattering-loss, refractive index modifications in lightly-fixed cat cornea and lens using 93 MHz repetition rate, 27 fs laser pulses with 0.3 nJ and 0.5 nJ pulse energies. These modifications were visible only using DIC microscopy and were not associated with apparent tissue damage. The resulting modifications correspond to refractive index changes between 0.05±0.001 and 0.021±0.001. Preservation of IRIS over a month of refrigerated storage suggested that the femtosecond laser-induced modifications were likely to involve relatively long-term molecular/structural alterations. In related experiments involving silicone hydrogels, the micromachined gratings (and associated Raman spectra) are stable for more than two years, even after drying and rehydration of the hydrogel.

In the spectral region around 400 nm, the human cornea starts absorbing slightly. At shorter wavelengths, this absorption becomes more significant. In a spectral window in the blue, the spectral response is minimal, yet the linear absorption is not is low enough not to cause photo-disruption of the tissue. Linear absorption in the cornea would cause unwanted attenuation of the excitation beam and unlocalized heating of the corneal tissue, which would result in cell death, which is undesirable. While the spectral region near 400 nm satisfies both requirements of minimized visual response as well as minimized linear absorption, forming of the refractive structures according to the embodied invention may be carried out between about 350 nm to about 600 nm within the defined focal region. An advantageous spectral range may be between about 375 nm to about 425 nm. Another advantageous spectral range may be between about 350 nm to about 400 nm.

A Laser and Optical Configuration For Modifying Ocular Tissue

Figure 3:
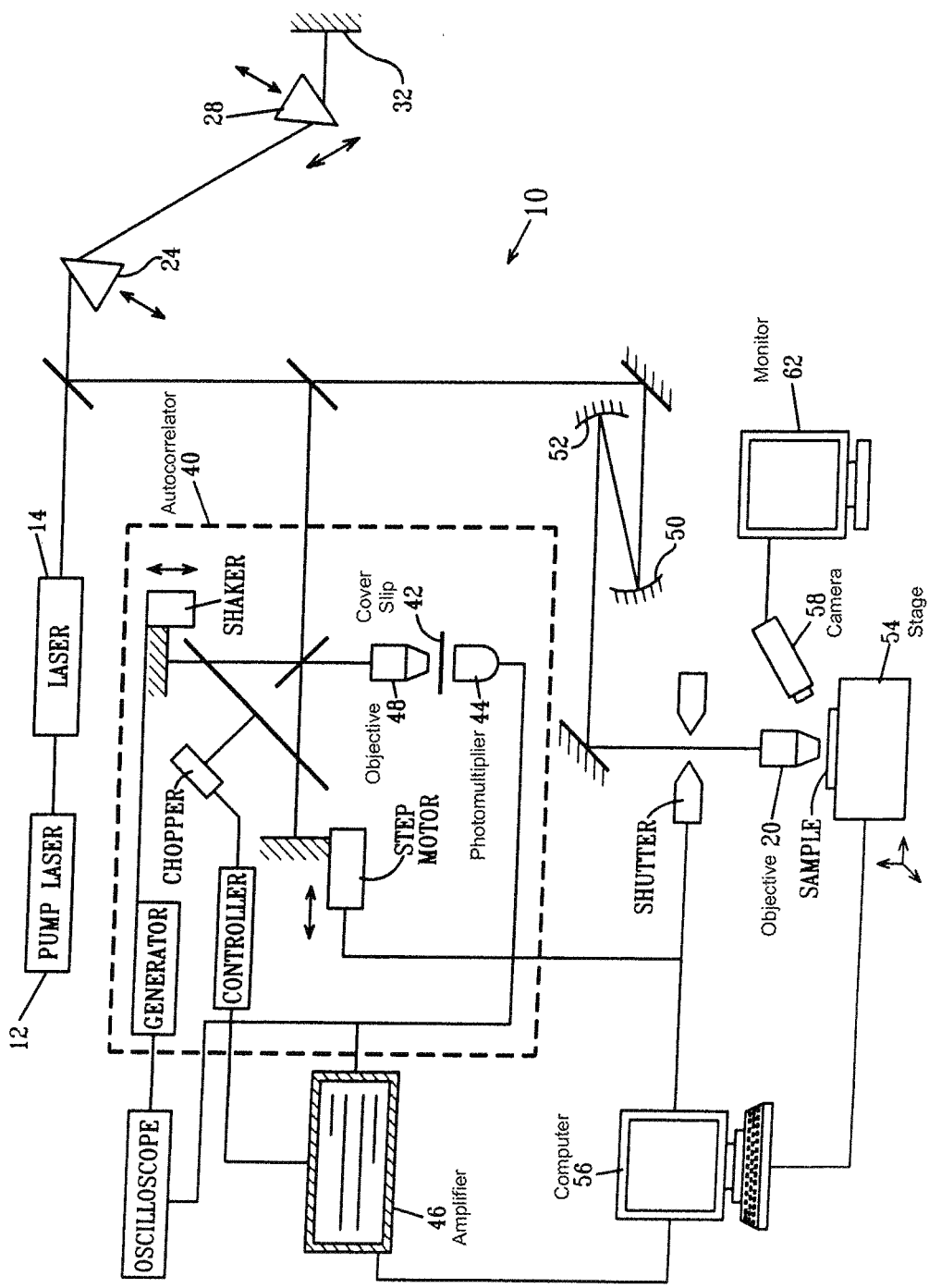
FIG. 3 is a schematic representation of the laser and optical system used to provide the refractive structures.

A non-limiting embodiment of a laser system 10 for irradiating ocular tissue with a laser to modify the refractive index of the tissue in select regions is represented in FIG. 3. A laser source comprises a Kerr-lens mode-locked Ti:Sapphire laser 12 (Kapteyn-Murnane Labs, Boulder, Colo.) pumped by 4 W of green light from a frequency-doubled Nd:YVO$_4$ laser 14. The laser generates pulses of 300 mW average power, 30 fs pulse width and 93 MHz repetition rate at wavelength of 800 nm. Because there is a reflective power loss from the mirrors and prisms in the optical path, and in particular, from the power loss of the objective 20, the measured average laser power at the objective focus on the material is about 120 mW, which indicates the pulse energy for the femtosecond laser is about 1.3 nJ.

The same laser source that is used to generate 800 nm femtosecond laser pulses directly above can also be used to generate a 400 nm femtosecond (fs) laser pulse using laser optical methods and devices well known in the art. For example, we have used the Kerr-lens mode-locked Ti:Sapphire laser to generate 400 nm fs laser pulses with an average laser power of about 80 mW, and a pulse duration of about 100 fs to form refractive structures within ocular tissues, e.g., corneal stroma. As stated, the use of the shorter wavelength laser pulse verses, for example, at 800 nm, allows one to create refractive structures at much greater scan speeds for a given change in refractive index of the tissue. Also, very importantly, the shorter wavelength laser pulse allows one to make much larger changes in the refractive index of the ocular tissue that was not possible at 800 nm without approaching the damage threshold of the tissue.

Due to the limited laser pulse energy at the objective focus, the pulse width must be preserved so that the pulse peak power is strong enough to exceed the nonlinear absorption threshold of the ocular tissue. Because the glass inside the focusing objective significantly increases the pulse width due to the positive dispersion inside of the glass, an extra-cavity, compensation scheme is used to provide the negative dispersion that compensates for the positive dispersion introduced by the focusing objective. Two SF10 prisms 24 and 28 and one ending mirror 32 form a two-pass one-prism-pair configuration. We used a 37.5 cm separation distance between the prisms to compensate the dispersion of the microscope objective and other optics within the optical path. A collinear autocorrelator 40 using third-order harmonic generation is used to measure the pulse width at the objective focus. Both 2nd and 3rd harmonic generation have been used in autocorrelation measurements for low NA or high NA objectives. We selected third order surface harmonic generation (THG) autocorrelation to characterize the pulse width at the focus of the high-numerical-aperture objectives because of its simplicity, high signal to noise ratio and lack of material dispersion that second harmonic generation (SHG) crystals usually introduce. The THG signal is generated at the interface of air and an ordinary cover slip 42 (Corning No. 0211 Zinc Titania glass), and measured with a photomultiplier 44 and a lock-in amplifier 46. After using a set of different high-numerical-aperture objectives and carefully adjusting the separation distance between the two prisms and the amount of glass inserted, we selected a transform-limited 27-fs duration pulse, which is focused by a 60×0.70 NA Olympus LUCPlanFLN long-working-distance objective 48.

Because the laser beam will spatially diverge after it comes out of the laser cavity, a concave mirror pair 50 and 52 is added into the optical path in order to adjust the dimension of the laser beam so that the laser beam can optimally fills the objective aperture. A 3D 100 nm resolution DC servo motor stage 54 (Newport VP-25XA linear stage) and a 2D 0.7 nm resolution piezo nanopositioning stage (PI P-622.2CD piezo stage) are controlled and programmed by a computer 56 as a scanning platform to support and locate the samples. The servo stages have a DC servo-motor so they can move smoothly between adjacent steps. An optical shutter controlled by the computer with 1 ms time resolution is installed in the system to precisely control the laser exposure time. With customized computer programs, the optical shutter could be operated with the scanning stages to micro-machine different patterns in the materials with different scanning speed at different position and depth and different laser exposure time. In addition, a CCD camera 58 along with a monitor 62 is used beside the objective 20 to monitor the process in real time.

The method and optical apparatus described above can be used to modify the refractive index of ocular tissue as follows. The first step in our micromachining experiment was to establish thresholds for the optical breakdown of lightly fixed feline cornea and lens cortex. The neutral density filter was first adjusted to minimize the focused incident laser power on the cornea and the lens below their breakdown thresholds. The incident laser power was then progressively increased by adjusting the neutral density filter. The breakdown threshold power was considered to be reached when visible plasma luminescence suddenly appeared and strong scattering light as well as laser-induced damage became visible, see FIGS. 4A to 4D and FIGS. 5A and 5B. Using the 0.70 NA long-working-distance objective in our system, the measured breakdown thresholds for cat cornea and lens was about 55 mW and 75 mW average laser power, respectively, which corresponds to a pulse energy of 0.6 nJ and 0.8 nJ, respectively.

Figure 4A:
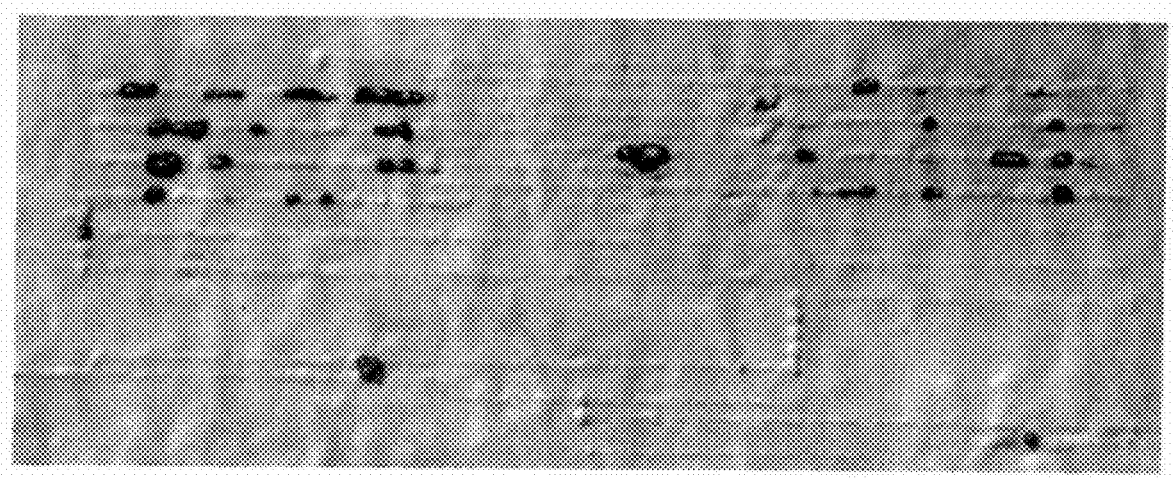
FIGS. 4A and 4C are Differential Interference Contrast (DIC) photographic images of a line grating in lightly-fixed cat corneal stroma at or near the tissue breakdown threshold.
Figure 4B:
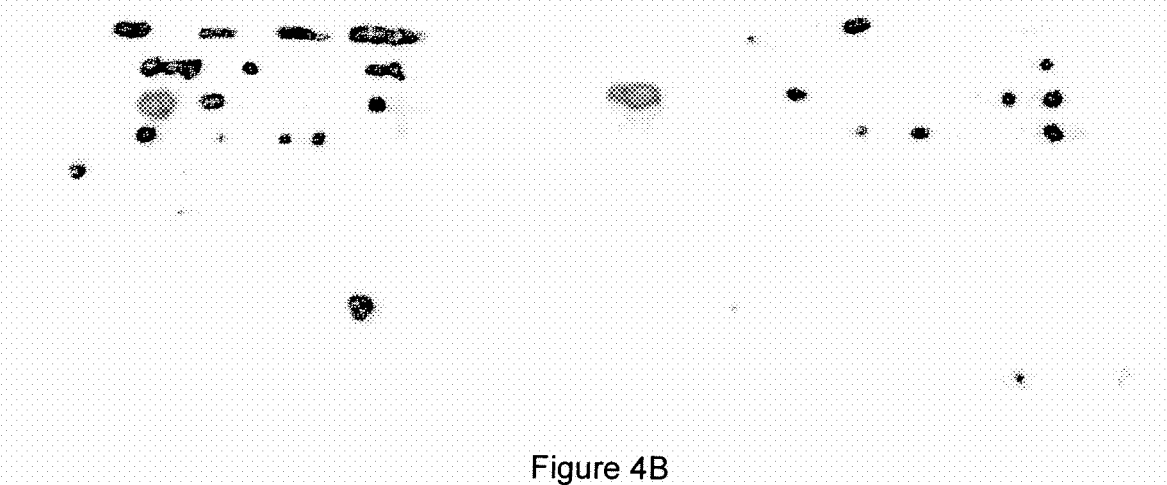
FIGS. 4B and 4D are Bright Field (BF) photographic images of a line grating in lightly-fixed cat corneal stroma at or near the tissue breakdown threshold.
Figure 4C:
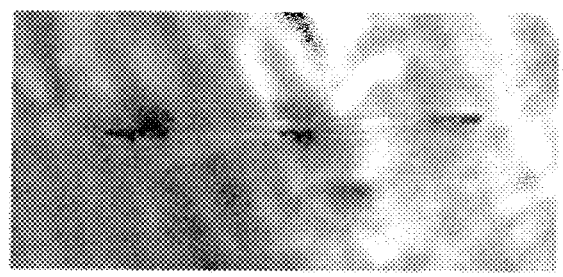
Figure 4D:
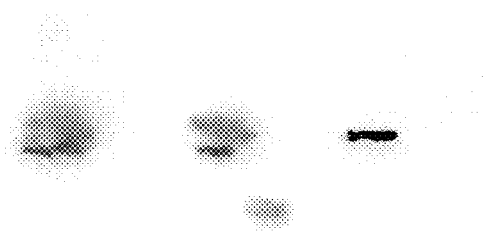
Figure 5A:
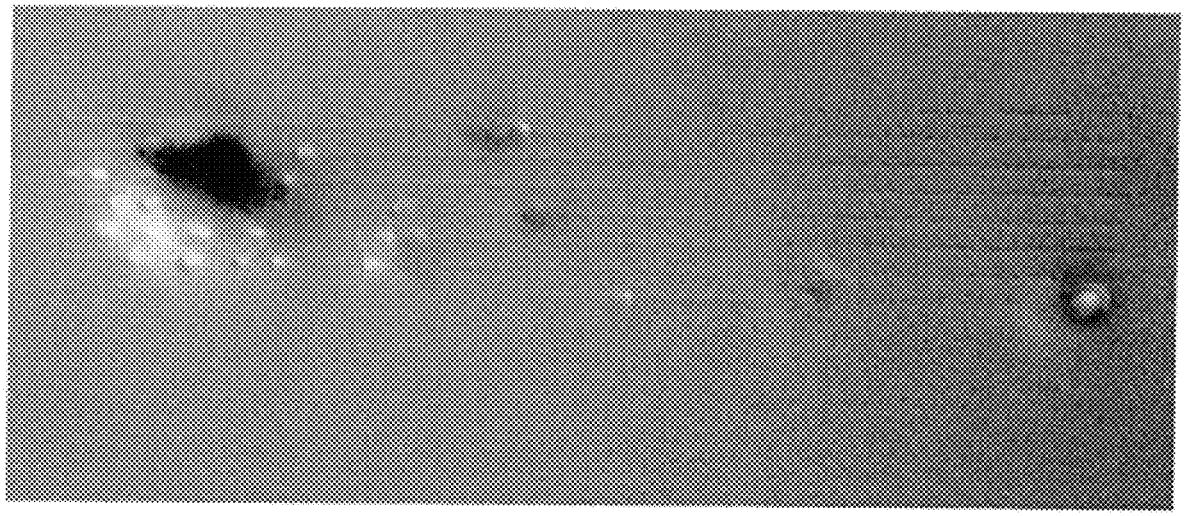
FIG. 5A is a DIC photographic image of a line grating in lightly-fixed cat lens cortex at or near the tissue breakdown threshold.
Figure 5B:
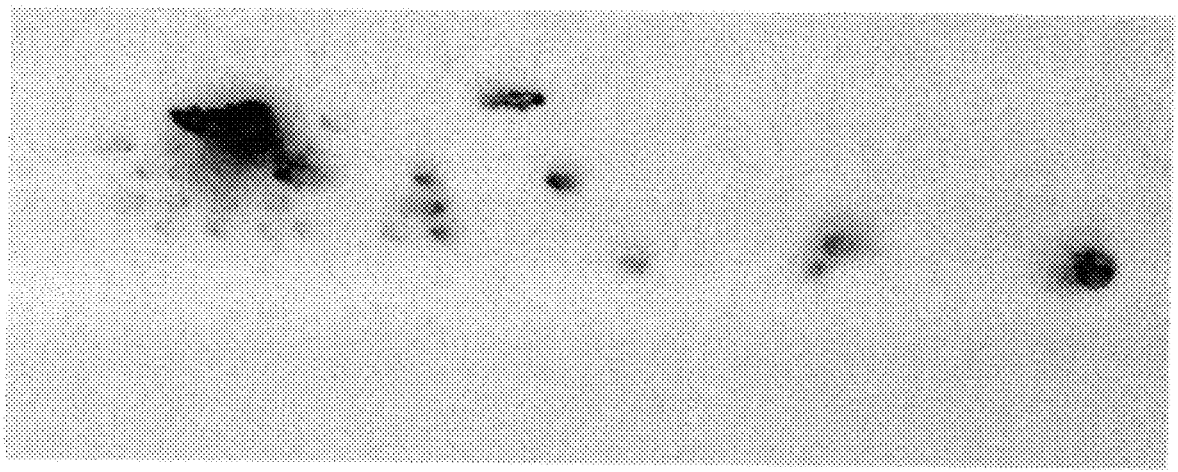
FIG. 5B is a BF photographic image of a line grating in lightly-fixed cat lens cortex at or near the tissue breakdown threshold.

FIGS. 4A to 4D are microscopic photographs of line gratings micromachined in lightly-fixed, cat corneal stroma using femtosecond laser conditions at or near the tissue breakdown threshold. FIGS. 4A and 4C are Differential Interference Contrast (DIC) images of lines created in the stroma of two different, lightly-fixed cat corneas with 0.6 nJ pulses and a scanning speed of 10 μm/s. Note, the spots of tissue destruction or "bubbles" (arrowed) along the micromachined lines (the clear, horizontal lines within stroma tissue). FIGS. 4B and 4D are Bright Field (BF) images of the same line gratings of FIGS. 4A and 4C, respectively. The BF images illustrate the visibility of tissue destruction (arrowed) and the relative invisibility of the rest of the lines that are clearly seen under DIC conditions.

Once tissue breakdown thresholds were established, the focused laser power was lowered gradually by carefully adjusting the neutral density filter until lines could be micromachined without the induction of bubbles or burns. We determined an average laser power setting of 30 mW for the cornea, which corresponds to a pulse energy of about 0.3 nJ.

The gratings were micromachined in the horizontal plane within the stroma of each corneal piece at a constant speed of 0.7 μm/s. The gratings consisted of 20-40 parallel lines, 100 μm long, 1 μm linewidth, 5 μm apart and about 100 μm beneath the corneal epithelium. Likewise, gratings were micromachined in the horizontal plane within the cortex of each lens at a constant speed of 1.0 μm/s. The gratings again consisted of 20-40 parallel lines, 100 μm long, 1 μm linewidth, 5 μm apart and about 100 μm beneath the lenticular surface. The spherical aberration at the laser focus induced by refractive index mismatch was compensated by an adjustable cover slip correction of the focusing microscope objective in order to achieve the smallest possible laser-affected region along the laser propagation direction.

Observation and Measurement of Refractive Index Change

After writing the observed structures in both corneal stroma and lens cortex we assessed whether the micromachined gratings are associated with a change in refractive index of the two different tissues. Immediately after micromachining, the slide containing the corneal piece and lens cortex was examined under an Olympus BX51 optical microscope. Bright field, phase contrast (PC) and differential interference contrast (DIC) were used to view the gratings. The slide was then moved to another setup where a low power 632.8 nm He—Ne laser was used to irradiate the gratings. The diffraction pattern from each grating was captured by a digital camera. The refractive index changes attained were calculated as described previously. See, Ding L, Blackwell R, Künzler J F, Knox W H, Large refractive index change in silicone-based and non-silicone-based hydrogel polymers induced by femtosecond laser micromachining, Optics Express 2006, 14, 11901-909.

In brief, the intensity of 0th order to 3rd order of diffracted light from the gratings was measured by a power meter. The different order diffraction efficiencies was obtained by calculating the ratios between the intensity of 1st, 2nd and 3rd to 0th order diffraction light. Because only one particular value of the refractive index change matches one particular diffraction efficiency value, one could calculate the index change within the femtosecond laser micromachined regions. We note that several factors could affect the results, such as the accuracy of measurement for the different diffraction order intensities, and the measurements of grating linewidth and thickness. To reduce measurement error of the diffraction order intensities, we took five measurements on each grating and calculated the average value and the standard deviation of the results. In principle, the spatial distribution of the refractive index change within the micromachined region was a small-scale gradient-index structure. For the purpose of this investigation, however, we presumed the index profile to be uniform within the grating lines, which were only 3 μm deep because the spherical aberration at the focal point was corrected.

The micromachined cat cornea and lens pieces were then removed from the glass slides after discarding the cover slips, and stored in the ethylene glycol/sucrose solution at 4° C. After one month, each corneal piece and lens piece was mounted onto a new glass slide for imaging and the diffraction light intensity measurement was repeated. This allowed us to assess whether the refractive index change initially observed had been maintained during storage.

Figure 6A:
FIG. 6A is a DIC photographic image of a line grating in lightly-fixed cat corneal stroma below the tissue breakdown threshold.
Figure 6B:
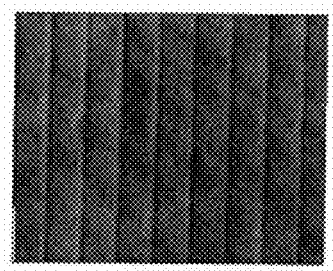
FIG. 6B is a zoomed-in DIC image of the line grating refractive structure shown in FIG. 6A.
Figure 6C:
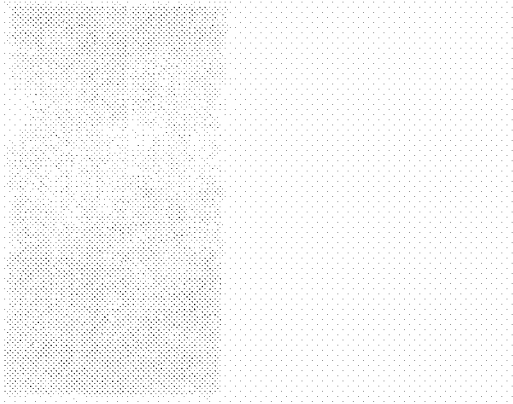
FIG. 6C is a BF photographic image of a line grating in lightly-fixed cat corneal stroma below the tissue breakdown threshold.

Exposure of lightly-fixed cat corneal to 0.3 nJ femtosecond laser pulses (30 mW average laser power) resulted in the reliable creation of grating patterns about 100 μm below the epithelial surface in all test samples, even when they were obtained from different cats. When imaged immediately after micromachining, individual grating lines could be clearly observed and distinguished with DIC microscopy (FIGS. 6A and 6B), but they were practically invisible when viewed under bright field transmission microscopy (FIG. 6C). This could be interpreted as the grating lines having very low scattering properties, which is in great contrast to the destructive tissue changes observed when laser energy was increased above the optical breakdown threshold levels (spots in FIG. 4). Using the knife-edge method, we ascertained that the laser focus diameter was 2.5 μm in air, which was much bigger than the micromachined line-widths.

Therefore, it appears that only the central part of the laser focal area had sufficient intensity to modify the refractive index of corneal tissue.

Figure 7A:
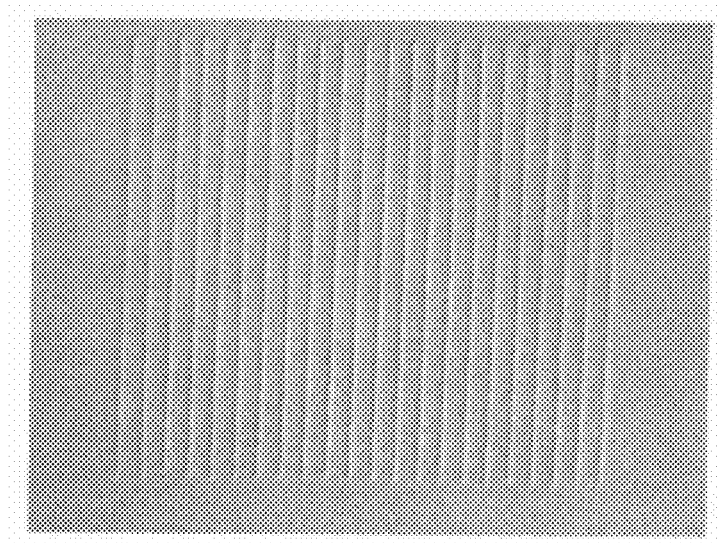
FIG. 7A is a DIC photographic image of a line grating in lightly-fixed cat lens cortex below the tissue breakdown threshold.
Figure 7B:
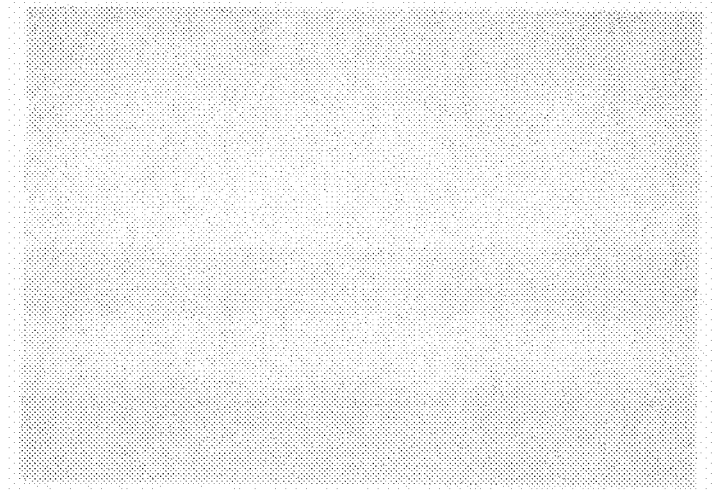
FIG. 7B is a BF photographic image of a line grating in lightly-fixed cat lens cortex below the tissue breakdown threshold.

Likewise, exposure of lightly-fixed cat lens cortex to 0.5 nJ femtosecond laser pulses (45 mW average laser power) resulted in the reliable creation of grating patterns about 100 µm below the lenticular surface in all test samples, even when they were obtained from different cats. When imaged immediately after micromachining, individual grating lines could be clearly observed and distinguished with DIC microscopy (FIG. 7A), but they were practically invisible when viewed under bright field transmission microscopy (FIG. 7B). Again, this is interpreted as the grating lines having very low scattering properties, which is in great contrast to the destructive tissue changes observed when laser energy was increased above the optical breakdown threshold levels (spots in FIG. 5). Also, it appears that only the central part of the laser focal area had sufficient intensity to modify the refractive index of lens cortex.

Figure 8A:
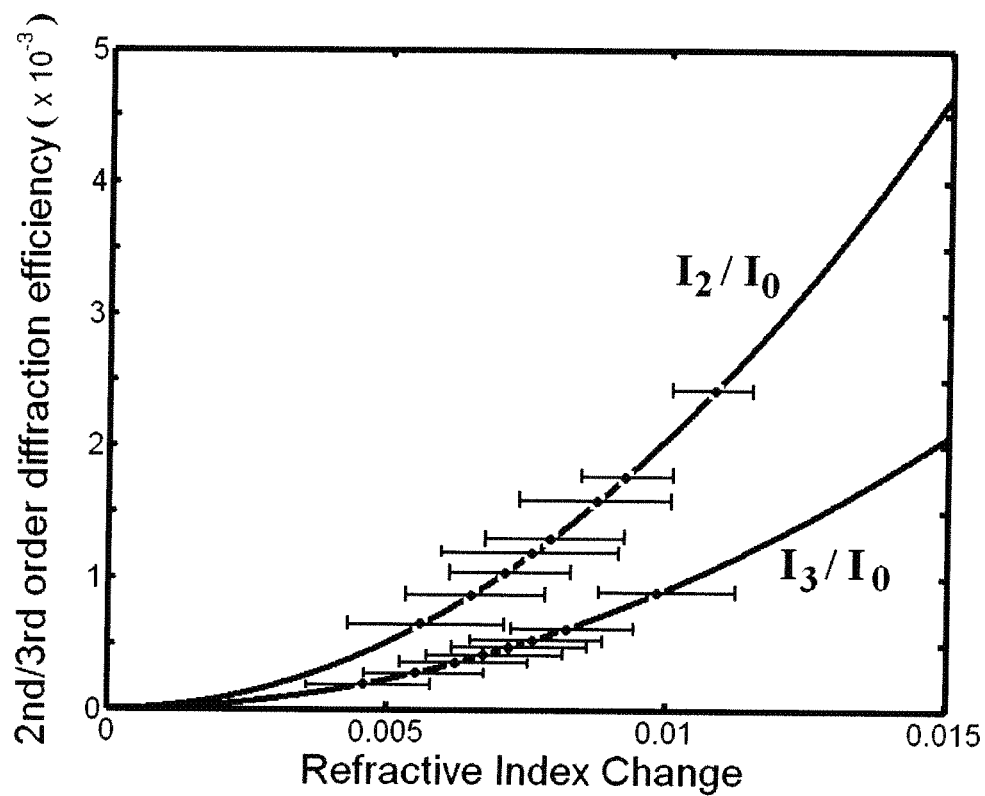
FIG. 8A is a graph plotting the 2nd and 3rd order diffraction efficiencies and the corresponding laser-induced refractive index changes of eight gratings micromachined in different corneal samples.
Figure 10A:
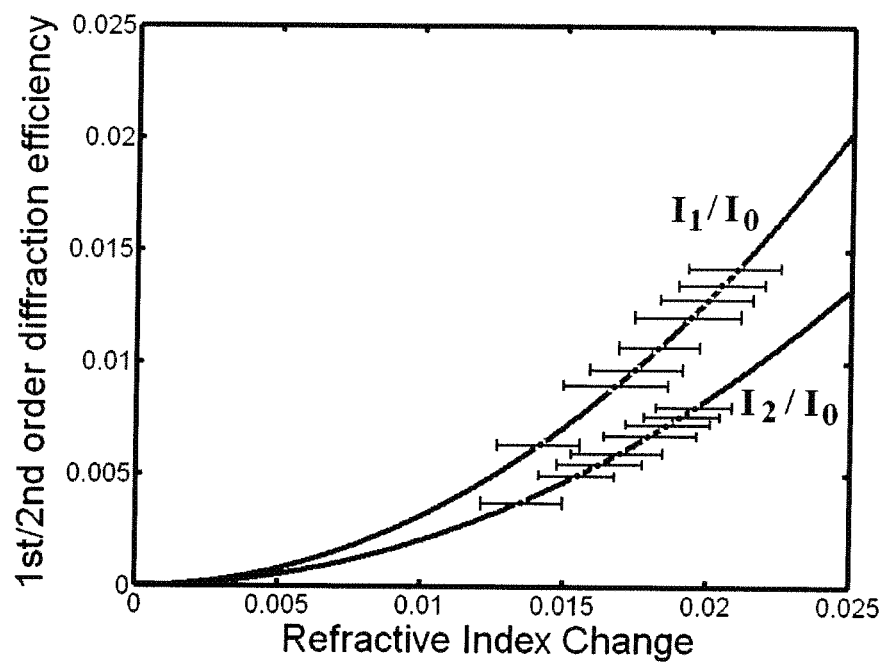
FIG. 10A is a graph plotting the 1st and 2nd order diffraction efficiencies and the corresponding laser-induced refractive index changes of eight gratings micromachined in different lens cortex samples.

In order to further assess the optical consequences of low-pulse-energy femtosecond laser micromachining on corneal stroma and lens cortex, we immediately irradiated the micromachined gratings with low power 632.8 nm He—Ne laser light. Because displacement of the stroma collagen lamellae as a result of post-mortem corneal swelling could not be completely avoided, scattering effect from the 0th order diffraction light was very strong, obscuring the 1st order diffraction light. Thus, only the 2nd and 3rd order diffraction efficiencies of each grating could be measured and used to calculate an approximate refractive index change within the femtosecond laser micromachined regions, FIG. 8A. In contrast, tissue swelling and opacification were minimal in slices of lens cortex, the 0th through 3rd order diffraction light could be measured clearly, and 1st and 2nd order diffraction efficiencies were used to calculate the induced change in refractive index (FIG. 10A).

Although a single diffraction efficiency is usually sufficient to calculate refractive index, we measured 1st/2nd or 2nd/3rd combinations to confirm that the refractive indices calculated were consistent through different diffraction orders. For these calculations, the average refractive indices of cat corneal stroma and lens were assumed to be 1.376 and 1.400, respectively. For corneal stroma, the calculated range of refractive index changes induced by the laser micromachining was from 0.005±0.001 to 0.01±0.001. For lens cortex, the calculated range of refractive index changes induced by the laser micromachining was from 0.005±0.001 to 0.03±0.001.

Figure 9A:
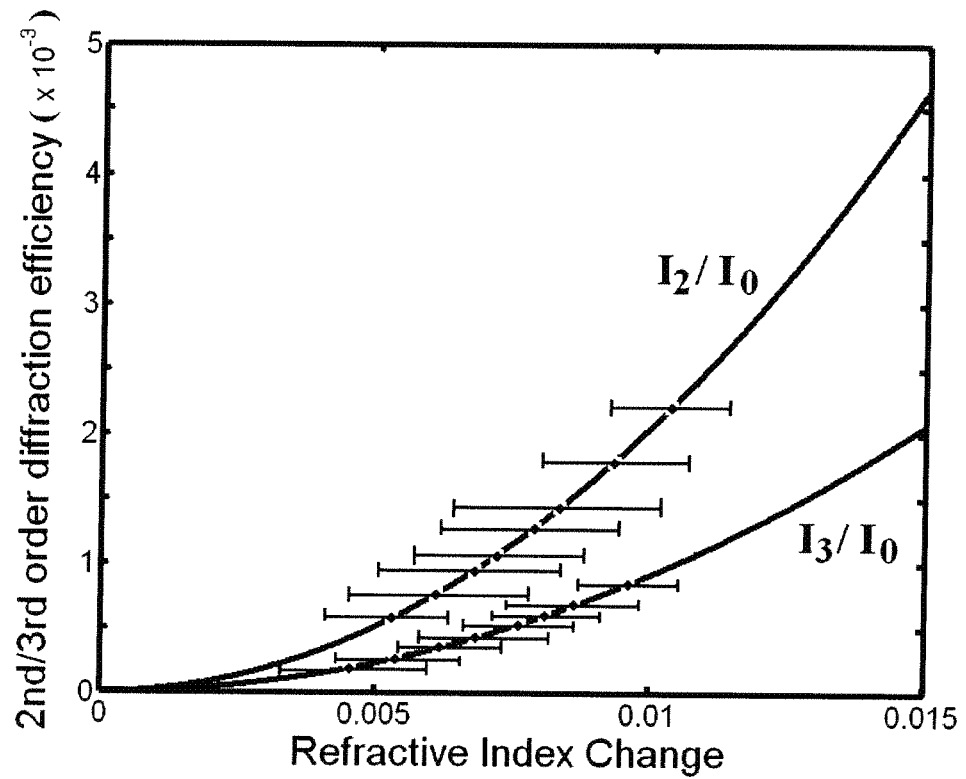
FIG. 9A is a graph plotting the 2nd and 3rd order diffraction efficiencies of eight gratings micromachined in different corneal samples after one month of storage.
Figure 9B:
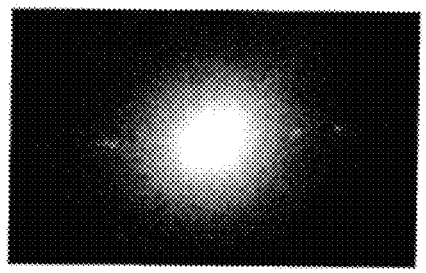
FIG. 9B is a photograph of the diffraction pattern obtained with a 632.8 nm He—Ne laser when illuminating the grating of FIG. 6A after one month.
Figure 11A:
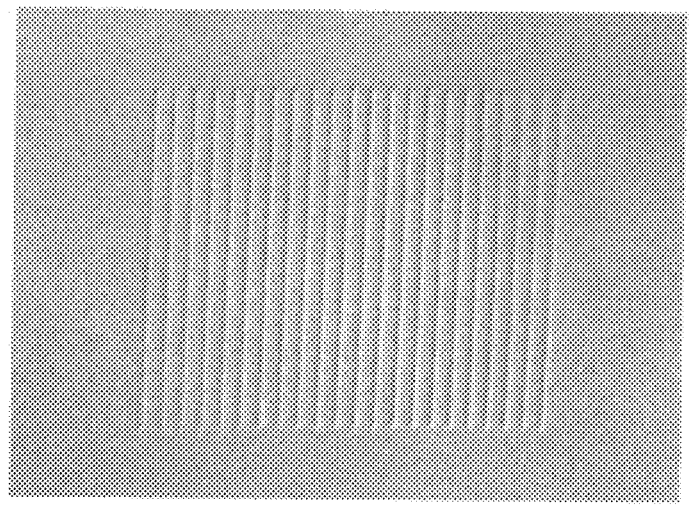
FIG. 11A is a DIC photograph showing the line grating of FIG. 7A after one month of storage.
Figure 11B:
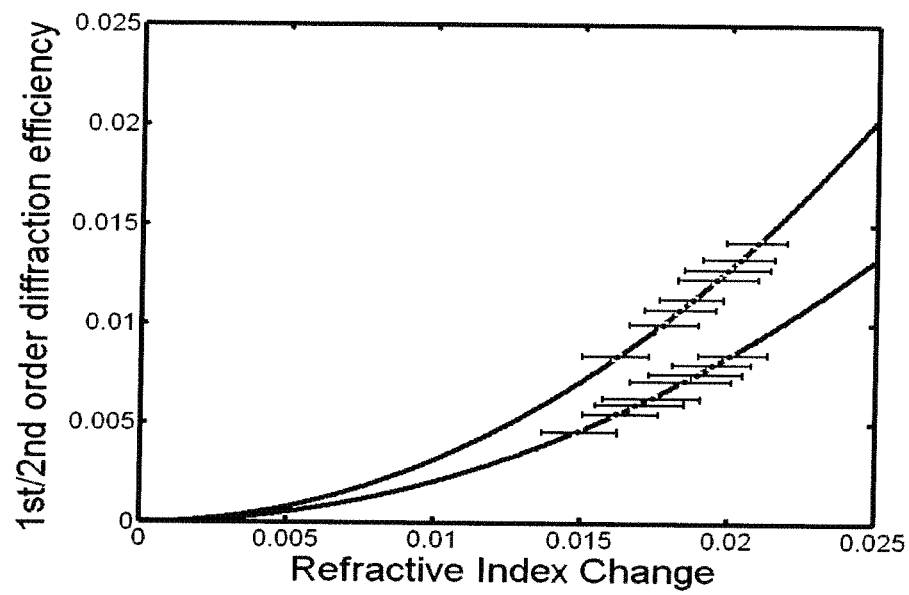
FIG. 11B is a graph plotting the 1st and 2nd order diffraction efficiencies of eight gratings micromachined in different lens cortex samples after one month of storage.

After undergoing low-pulse-energy femtosecond laser micromachining, each cornea piece was returned to the storage solution in a −20° C. freezer for one month in order to determine if the micromachined structures could be maintained over such a period of time. After one month, the cornea pieces were removed from storage and re-examined. The storage solution significantly slowed corneal swelling and opacification (relative to conventional storage in 0.1M PBS, for example), but was not able to completely prevent these events. In spite of a moderate loss of corneal transparency, DIC microscopy did reveal that the grating structures initially micromachined into the corneal stroma were still present one month after they were originally created as demonstrated by the diffraction pattern observed in FIGS. 7B and 9B. The edges of the lens slices became opaque following one month storage, but the centers remained largely transparent and the micromachined gratings were still clearly visible in a DIC image, FIG. 11A.

Figure 8B:
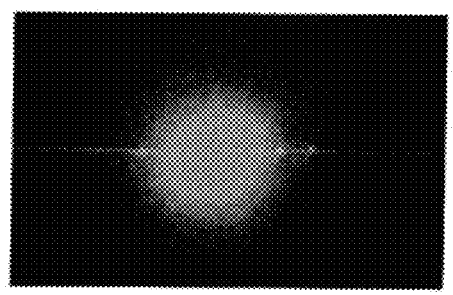
FIG. 8B is a photograph of the diffraction pattern obtained with a 632.8 nm He—Ne laser when illuminating the grating of FIG. 6A
Figure 10B:
FIG. 10B is a photograph of the diffraction pattern obtained with a 632.8 nm He—Ne laser when illuminating the grating of FIG. 7A.
Figure 11C:
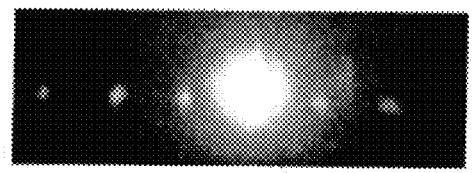
FIG. 11C is a photograph of the diffraction pattern obtained with a 632.8 nm He—Ne laser when illuminating the grating of FIG. 7A after one month.

The diffraction light distribution of one-month old gratings in corneal stroma (FIG. 9B) was again measured and found to be no different than that obtained right after the gratings' creation (FIG. 8B). Also, the diffraction light distribution of one-month old gratings in lens cortex (FIG. 11C) was again measured and found to be no different than that obtained right after the gratings' creation (FIG. 10B). In the corneal pieces, the scattering light from the 0th order diffraction still obscured the 1st order diffraction. However, the 2nd, 3rd, and even 4th order diffractions were still visible and easy to measure. In the case of the 800 nm work, the measured refractive index change after one month of storage remained from 0.005±0.001 to 0.01±0.001 for the corneal pieces and from 0.005±0.001 to 0.03±0.001 for the lens pieces.

Applications in ophthalmic surgery will now be described. As shown in FIGS. 4A to 4C, it is possible to write micron-scale features into the corneal stroma with minimal scattering loss by carefully controlling the laser and scan parameters such as pulse width, average power, repetition rate, scan rate and focusing conditions. This result, which is significantly different than the results in corneal surgery that have been previously reported using femtosecond, focused pulses, suggests to us certain applications.

One such application is in writing fiducial marks in the corneal stroma. More particularly, in one application involving excimer laser ablation of the cornea for vision correction—laser in situ keratomileusis or LASIK—it is first necessary to cut across the cornea with a 'flap cutting' device. Typically, a rapidly vibrating razor blade or microkeratome is used for this purpose. This method generally produces acceptable results, however the depth of the final cut is not precise, and sometimes the degree of accommodation that can be achieved with excimer laser ablation is compromised. A competing form of corneal flap-cutting involves the use of a high-power, femtosecond laser. Femtosecond flap cutting has not yet been widely adopted in clinical refractive surgery practices, in part because of uncertainty about the long-term photochemical, mechanical and biological effects of this technique. Recently, there have been reports about negative effects of this technique, particularly in terms of tissue destruction, which appears significantly stronger than that obtained following microkeratome cutting.

Figure 12:
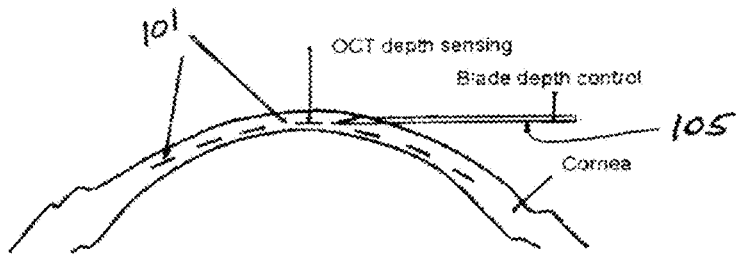
FIG. 12 is a schematic representation of a use of the preferred or another embodiment in providing fiducial marks in the cornea.

The micromachining process described provides a possible solution to the problem of being able to make a precise cut in the corneal stroma without additional tissue destruction. FIG. 12 shows a situation in which fiducial marks 101 has been machined into the stroma of the cornea, for example, at a specific location and depth. Low-energy femtosecond laser pulses can be used to write fiducial marks 101 in the stroma of the cornea at a specific depth and location. The fiducial mark 101 would not be visible to a human, as indicated by FIGS. 4b and 4D, however it is detectable by specialized optical techniques such as Optical Coherence Tomography (OCT) or Differential Interference Contrast (DIC) microscopy (FIGS. 4A and 4C).

The fiducial marks 101 could be used to 'lock' the depth of the cutting blade by using an imaging technique such as Optical Coherence Tomography (OCT). OCT has been well developed for both retinal and corneal imaging. This would ensure that the resulting depth of the blade cut would be significantly better regulated than is currently possible, even if a femtosecond laser is used to cut the corneal flap. The location and depth of a fiducial mark 101 is obtained using optical coherence tomography (OCT) interfaced with blade control, and the depth of the blade 105 is 'locked' to this depth and 'guided' along a specified cutting path, which can ensure accurate flap cutting.

Another application is in altering the optical power of the cornea. Currently, laser refractive surgery achieves changes in the optical power of the cornea by destroying/removing corneal tissue. Tissue destruction causes (1) a change in the surface profile (and curvature) of the cornea, (2) a change in corneal biomechanical properties (usually a flattening of the corneal surface), and (3) a wound healing response. A change in surface shape of the cornea as a result of points (1) and (2) is sufficient to correct large optical aberrations such as defocus and astigmatism. However, as mentioned earlier, the wound healing response that results from corneal tissue destruction limits current laser refractive procedures by decreasing their ultimate optical benefit. Exemplary femtosecond micromachining patterns that could be written into the corneal stroma include a continuous circular area, an annulus pattern, or a segmented annulus pattern.

The use of femtosecond laser pulses as described to modify the optical power of the cornea can be accomplished as follows: (1) by changing the refractive index of the cornea stroma, and (2) by altering corneal biomechanics without inducing a significant corneal wound healing response. Because of the femtosecond laser's ability to be focused non-invasively, in a non-contact manner, to effect at any chosen depth within the cornea stroma, this procedure would not require removal of the corneal epithelium or creation of a corneal flap. Epithelial manipulations are one of the major stimuli causing the wound healing response since such manipulations destroy the normally close interaction (both physically and biologically) of the corneal epithelium with its underlying stroma. The femtosecond micromachining (i.e. use of low-energy femtosecond pulses to alter tissue properties non-destructively) could be applied over a continuous area, 6-8 mm in diameter, in the center of the cornea or at particular locations in the corneal periphery as mentioned above, depending on the optical or biomechanical changes desired.

The micromachining process described also provides an opportunity for an ocular surgeon to modify the refractive index of the corneal stroma layer of a patient having undergone cataract surgery. The method allows the ocular surgeon to correct any aberrations as a result of the surgery. For example, starting from a lens of selected power, the power of which will vary according to the ocular requirements of the patient, the surgeon can subsequently adjust the refractive properties of the corneal stroma layer to correct a patient's vision based upon the individual needs of the patient. In essence, an intraocular lens would essentially function as a fixed power lens to correct for the refractive error of a patient's eye. The patient's vision can then be further adjusted post-implantation by modifying the refractive index of select regions of the patient's corneal stroma layer. As a result, post-operative refractive errors resulting from pre-operative measurement errors, variable lens positioning during implantation and wound healing (aberrations) can be corrected.

For instance, cataract surgery typically requires that the natural lens of each eye be replaced with an intraocular lens (TOL). Following insertion of the IOL the surgeon or eye specialist can correct for aberrations resulting from the surgery or correct for slight misplacement of the IOL. Following surgery, and after allowing time for the wound to heal, the patient would return to the surgeon to have select regions of his or her corneal stroma layer irradiated. These irradiated regions would experience a change in refractive index, which would correct for the aberrations as well as the patients needs for vision correction.

Accordingly, the invention is directed to a method comprising identifying and measuring the aberrations resulting from the surgical procedure. Once the aberrations are identified and quantified using methods well known in the art of ophthalmology, this information is processed by a computer. Of course, information related to the requisite vision correction for each patient can also be identified and determined, and this information can also be processed by a computer. There are a number of commercially available diagnostic systems that are used to measure the aberrations. For example, common wavefront sensors used today are based on the Schemer disk, the Shack Hartmann wavefront sensor, the Hartmann screen, and the Fizeau and Twymann-Green interferometers. The Shack-Hartmann wavefront measurement system is known in the art and is described in-part by U.S. Pat. Nos. 5,849,006; 6,261,220; 6,271,914 and 6,270,221. Such systems operate by illuminating a retina of the eye and measuring the reflected wavefront.

Once the aberrations are identified and quantified, the computer programs determine the position and shape of the optical structures to be written into the corneal stroma to correct for those aberrations. These computer programs are well known to those of ordinary skill in the art. The computer than communicates with the laser-optical system and select regions of corneal stroma are irradiated with a focused, visible or near-IR laser having a pulse energy from 0.01 nJ to 1.0 nJ. Alternatively, one can use 400 nm laser light with a similar pulse energy to generate even greater changes in the refractive index of corneal stroma.

The described micromachining process can also be used for custom vision correction of higher order wavefront aberration in the optical path of the eye. The basic technology for detecting and correcting aberrations of at least third-, fifth-, and tenth orders is taught in U.S. Pat. No. 5,777,719, whose disclosure is hereby incorporated by reference in its entirety into the present disclosure. Given that the region of refractive index change generated by femtosecond laser micromachining can be as small as 1 µm in diameter, this will make it possible to correct small, localized optical wavefront aberrations (higher order aberrations) in the optical path of the eye. Such aberrations exist both naturally, or can be induced by ocular surgeries, such as laser refractive surgery, corneal transplantation and wound healing following trauma to the eye.

Figure 13A:
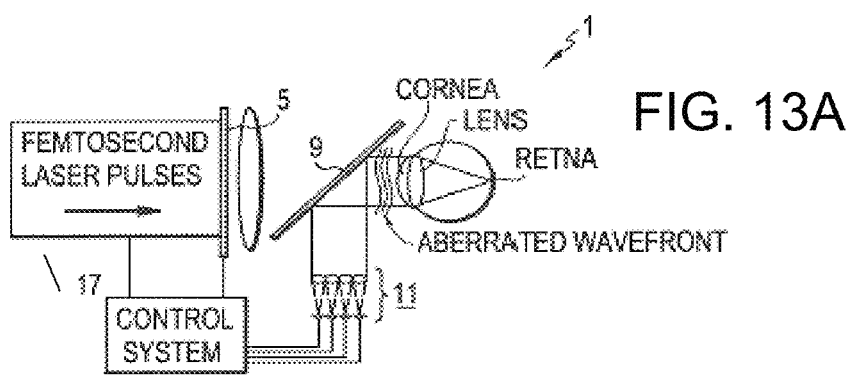
FIGS. 13A-13C are schematic diagrams of a device in which the preferred or another embodiment can be implemented.
Figure 13B:
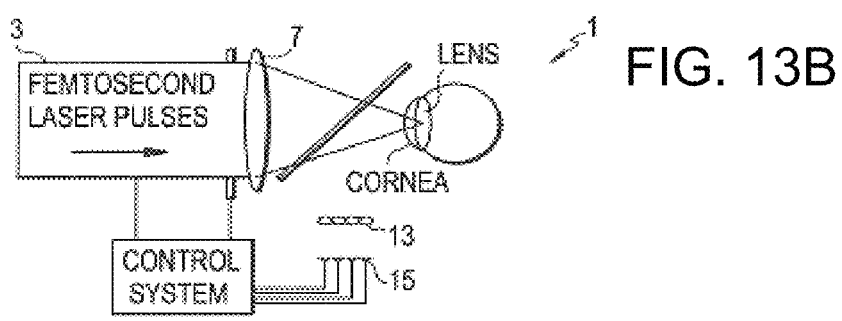
Figure 13C:
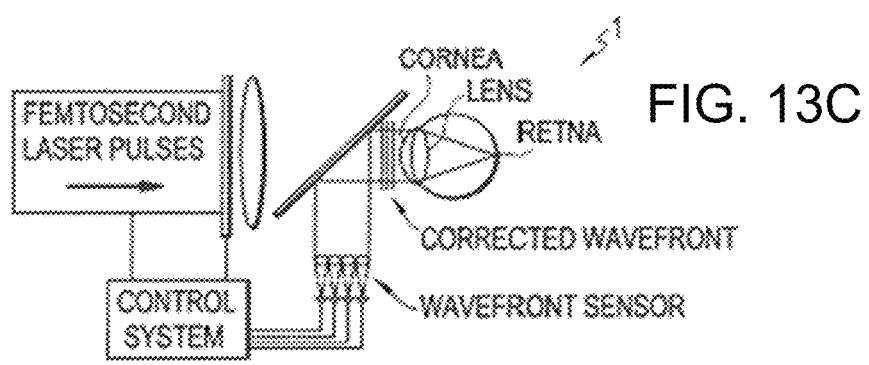

FIGS. 13A to 13C show a schematic diagram of a device 1 used to carry out the preferred embodiment or another embodiment. The device 1 includes a laser 3 for emitting femtosecond laser pulses, a shutter 5, a focusing lens 7, a dichroic mirror 9, a wavefront sensor 11 having a lenslet array 13 and a detector array 15, and a control system 17 for controlling the operations described herein.

As illustrated in FIGS. 13A to 13C, the process we propose would include the following steps: (1) using a wavefront sensor to detect and measure the lower and higher order aberrations along the optical path of a given eye, (2) calculating the topography and magnitude of refractive index changes required to achieve the necessary aberration correction, (3) focusing the femtosecond laser pulses either into the cornea or intraocular lens in order to carry out the micromachining necessary to induce the required refractive index change. Once the micromachining is complete, the wavefront sensor would be used once again to check the correction of the ocular wavefront. Since the resolution of the femtosecond laser micromachining is about 1 µm, this noninvasive method could be used as a complement or an alternative method for current customized wavefront correction methods.

In FIG. 13A, the shutter 5 is closed for detection of wavefront aberration from the optical path through the wavefront sensor 11, using aberrated light reflected from the retina of the eye. In FIG. 13B, the shutter 5 is open, and light pulses from the femtosecond laser 3 are used to correct the aberration by locally changing the index in the cornea or the lens of the eye. In FIG. 13C, after femtosecond laser 3 micromachining, the wavefront correction is verified once again using the wavefront sensor 11.

Calculation of Change in Refractive Index

As mentioned. these gratings were investigated by focusing an unpolarized He—Ne laser beam with a wavelength of 632.8 nm on these gratings and monitoring the diffraction pattern. The diffraction angles showed good agreement with the diffraction equation $m\lambda = d \sin \theta$ (1)

where m is the diffraction order, $\lambda$ is the wavelength of the incident laser beam which here is 632.8 nm, and d is the grating period.

The diffraction efficiency of the grating can be measured, and since the efficiency is a function of the refractive index change, it may be used to calculate the refractive index change in the laser irradiation region. Consider the grating as a phase grating, its transmittance function could be written as $$t(x_0, y_0) = (e^{i\phi_2} - e^{i\phi_1}) rect\left(\frac{x_0}{a}\right) * \frac{1}{d} comb\left(\frac{x_0}{d}\right) + e^{i\phi_1} \quad (2)$$

where a is the grating line width, d is the groove spacing, $\phi_2$ and $\phi_1$ are the phase delays through the lines and ambient region respectively, $$\phi_2 = 2\pi \times \frac{(n+\Delta n) \times b}{\lambda} \text{ and } \phi_1 = 2\pi \times \frac{n \times b}{\lambda},$$

b is the thickness of the grating line, n is the average refractive index of the material, $\Delta n$ is the average refractive index change in the grating lines, and $\lambda$ is the incident light wavelength of the measurement (632.8 nm). Here, the grating line width is 1 μm and the thickness is 3 μm. The index change within the laser effect region can be approximated to be uniform. The convolution theorem can be used to calculate the spectrum of the grating such as $$T(f_x, f_y) = F\{t(x_0, y_0)\} = (e^{i\phi_2} - e^{i\phi_1}) a \sin c(af_x) comb (df_x)\delta(f_y) + e^{i\phi_1}(f_x, f_y) \quad (3)$$

(where the term written as 'sin c' is the 'sin c' function sin x/x).

Then, the intensity distribution of the grating diffraction pattern is:

$$I(x, y) = \left(\frac{1}{\lambda z}\right)^2 \times$$

$$\left[(e^{i\phi_2} - e^{i\phi_1})\frac{a}{d}\sum_{n=-\infty}^{\infty} \text{sinc}\left(\frac{an}{d}\right)\delta\left(\frac{x}{\lambda z}-\frac{n}{d}, \frac{y}{\lambda z}\right) + e^{i\phi_1}\delta\left(\frac{x}{\lambda z}, \frac{y}{\lambda z}\right)\right]^2 \quad (4)$$

From this formula, the intensity of the 0th (I0), 1st (I1), and 2nd (I2) order diffraction light is $$I_0 = \left(\frac{1}{\lambda z}\right)^2 \times \left[\left(e^{i2\pi \times \frac{(n+\Delta n) \times b}{\lambda}} - e^{i2\pi \times \frac{n \times b}{\lambda}}\right)\frac{a}{d} + e^{i2\pi \times \frac{n \times b}{\lambda}}\right]^2 \quad (5)$$

$$I_1 = \left(\frac{1}{\lambda z}\right)^2 \times \left[\left(e^{i2\pi \times \frac{(n+\Delta n) \times b}{\lambda}} - e^{i2\pi \times \frac{n \times b}{\lambda}}\right)\frac{a}{d}\text{sinc}\left(\frac{a}{d}\right)\right]^2 \quad (6)$$

and $$I_2 = \left(\frac{1}{\lambda z}\right)^2 \times \left[\left(e^{i2\pi \times \frac{(n+\Delta n) \times b}{\lambda}} - e^{i2\pi \times \frac{n \times b}{\lambda}}\right)\frac{a}{d}\text{sinc}\left(\frac{2a}{d}\right)\right]^2 \quad (7)$$

By comparing the light intensities of $1^{st}$, $2^{nd}$ and $0^{th}$ diffraction orders, the refractive index change within the grating lines can be determined.

EXAMPLES

Extraction and Preparation of Cat Corneas

Eight corneas and eight lenses were extracted under surgical anesthesia from five normal, adult domestic shorthair cats (felis cattus). All animal procedures were conducted in accordance with the guidelines of the University of Rochester Committee on Animal Research, the ARVO Statement for the Use of Animals in Ophthalmic and Vision Research, and the NIH Guide for the Care and Use of Laboratory Animals. Feline corneas and lenses were chosen because of their similarity to human corneas and lenses in terms of histological structure, molecular composition and optical properties. See, Hughes A. The topography of vision in mammals of contrasting life style: comparative optics and retinal organization. Handbook of Sensory Physiology, VII/5. Berlin: Springer Verlag; 1977. Also, in contrast with the problems associated with obtaining post-mortem human eyes, using cat corneas and lenses allowed us to precisely control post-mortem extraction time and tissue processing parameters. This was important to avoid degradation and opacification of the corneas and lenses prior to femtosecond laser micromachining. Extracted feline tissues were immediately drop-fixed for 10 minutes (corneas) in a solution consisting of 1% paraformaldehyde in 0.1M phosphate buffered saline (PBS), pH 7.4. Lenses were cut into 500 μm thick slices using a vibratome. The lens slices and whole corneas (~500 μm thick) were immersed in a mixture of 30% ethylene glycol+30% sucrose in 0.1M PBS, pH 7.4 at 4° C. The ocular tissues were stored in this solution at all times in order to minimize tissue swelling and loss of transparency.

Femtosecond Laser Micromachining

For laser micromachining, the corneas were trimmed to generate small, flat pieces of tissue, averaging ~1 cm². Each piece of cornea was then flattened onto a clear glass slide (1×3 inches, 1 mm thick, Surgipath Medical Industries Inc., Ill.) with the epithelium facing up and the endothelium facing down. A glass coverslip (Corning No. 0211 Zinc Titania glass) was placed on the top of each piece of cornea or lens, stabilizing it for the duration of the experiment. The ethylene glycol/sucrose storage solution was used as mounting medium to prevent or at least minimize dehydration of the cornea and lens since these effects are known to alter the refractive index and transparency of both these tissues.

Example 1

Femtosecond laser micro-machining was conducted as previously described in U.S. patent application Ser. No.

11/745,746, filed May 8, 2007 and U.S. patent application Ser. No. 11/948,298, filed Nov. 30, 2007. The laser source was a Kerr-lens mode-locked Ti:Sapphire laser (K-M Labs). This laser oscillator generates pulses averaging 300 mW, pulse duration of 27 fs and a 93 MHz repetition rate at 800 nm wavelength. A continuously variable, metallic, neutral density filter was inserted into the optical path and used to adjust the incident laser power onto each cat cornea piece. The femtosecond laser pulses were focused 100 µm below the tissue surface using a 60×, 0.70 NA Olympus LUCPlan-FLN long-working-distance microscope objective. Because the large amount of glass within the microscope objective induces significant chromatic dispersion into the femtosecond laser pulses, greatly broadening the femtosecond pulse durations, we used a standard extra-cavity-prism double-pass configuration to compensate for the dispersion and maintain the ultrashort pulse duration. By carefully adjusting this dispersion compensator, we obtained nearly transform-limited 27 fs duration pulses at the focal point of the focusing objective which were measured by a collinear autocorrelator using 3rd order surface harmonic generation (THG). During femtosecond laser micromachining, the slide containing the biological tissue samples was mounted on a 3D scanning platform consisting of a Physik Instrumente (PI) P-622.2CD XY scanning stage with 250 µm travel range and 0.7 nm close-loop resolution, and a Newport VP-25XA linear servo Z-axis scanning stage with 25 mm travel range and 100 nm resolution. An infrared CCD camera was used to monitor the micromachining process and the generation of visible plasma luminescence in real-time.

Our experiments were conducted at room temperature (~25° C.). It took about 40 minutes to create a (100 µm×50 µm) grating and conduct the immediate post-micromachining measurements. Corneal trimming and mounting did not exceed 10 minutes in duration, and the corneal tissue was exposed to ambient air during the trimming process for at most 2 minutes. Application of the Ti:Sapphire femtosecond as described resulted in the formation of micromachined gratings having 20 to 40 lines into the stroma of the corneas; each line approximately 1 µm wide, 100 µm long and 5 µm apart. Refractive index changes in the micromachined regions were calculated immediately and after one month of further storage by measuring the intensity distribution of diffracted light when the gratings were irradiated by 632.8 nm wavelength He—Ne laser light. Because we observed no significant changes in cornea and lens transparency or thickness at the end of our micromachining experiments, we conclude that the described micromachining process did not cause significant corneal or lenticular dehydration or swelling.

Example 2

Irradiation of Cat Corneas at 400 nm

Figure 14:
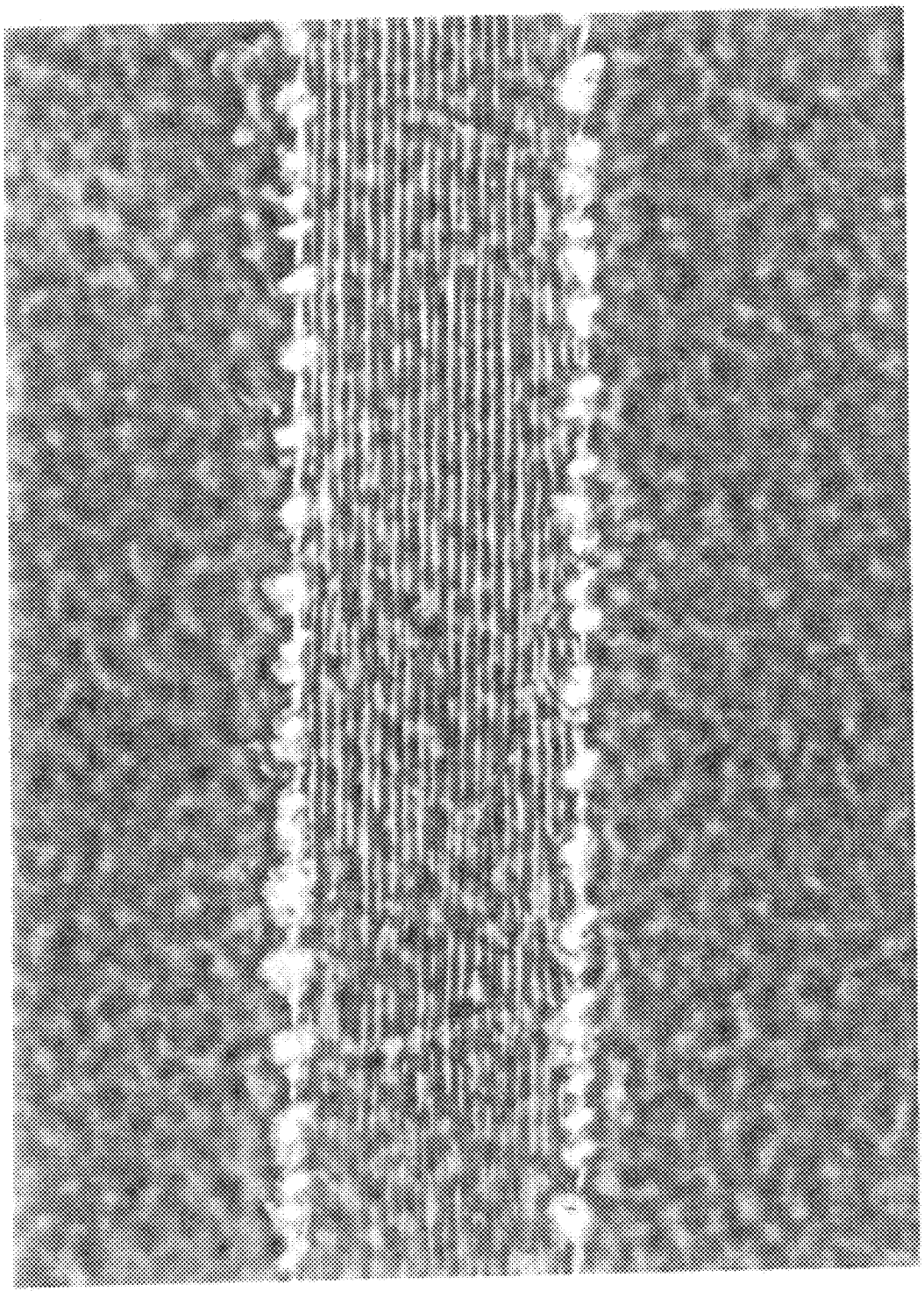
FIG. 14 is a phase contrast photographic image of a line grating in cat corneal stroma below the tissue breakdown threshold (middle line pattern) bordered by damage lines using 800 nm femtosecond laser pulses.

Using the laser system described in Example 1 but doubling the wavelength of the light to 400 nm and making slight changes in other laser operating parameters one is able to dramatically increase the process efficiency for the formation of refractive structures in cat corneas. In one embodiment, we formed a series of refractive (line) gratings with a line spacing of 5 µm about 150 µm from the top surface of the cornea with Ti:Sapphire femtosecond laser above. The average laser power was 80 mW, the pulse duration was about 100 fs and we varied the scan speed from 1 mm/s to 15 mm/s. At the slower speeds, i.e., 1 and 2 mm/s, we observed some damage to the cornea tissue, particularly at 1 mm/s scan speed. Increasing the scan speed to 5, 10 or even 15 mm/s provided refractive structures that could only be observed using a phase contract adjustment to the photomicrograph. The measured change in the refractive index of the focal regions for the 5, 10 and 15 mm/s scans were .037, 0.03 and 0.22, respectively. FIG. 14 is a phase contrast micrograph of a refractive structure in the form of a line grating described above that was obtained at a scan speed of 15 mm/s.

To determine the degree of physical change or potential damage (cell death) to the corneal stroma by the micromachining process described on can use In vivo confocal microscopy (IVCM), first described by Minsky. See, Minsky M., Memoir on inventing the confocal microscope. *J Scanning* 10, 128-138 (1988). IVCM allows in vivo examination of the human cornea and conjunctiva at the cellular level. IVCM is able to demonstrate the characteristic corneal and conjunctival anatomy in vivo at the cellular level. Normal corneal innervation and cell distribution, as well as changes associated with age, contact lens wear and systemic disease such as diabetes can be documented in vivo with this technique. IVCM has been used to evaluate postsurgical procedures including refractive surgery, UV-crosslinking, keratoplasty and amniotic membrane transplantation to evaluate corneal wound healing. Several principles are realized in confocal microscopes: tandem-scanning, scanning-slit and laser-scanning confocal microscopy. Although it has high axial and transverse resolution, tandem-scanning IVCM is not able to visualize specific structures in the cornea, such as basal epithelial cells, due to its low light throughput. However, it may be superior when scanning the corneal endothelium.

Another minimally invasive technique that can be used to assess physical changes in the corneal stroma as a result of the described micromachining process is the combination of reflective confocal microscopy with multiphoton microscopy first reported by Denk et al., *Science* 1990, 73-76. See, Dong, Chen-Yuan, et al., *Microscopy Research and Technique* 2008, 71, 83-85. The two imaging modalities allow detection of complementary information from the cornea. The assessment of epithelial cellular boundaries and nuclei, the Bowman's layer and the keratocytes can be detected in the reflected confocal imaging mode, whereas the epithelial cell cytoplasm and the structural collagen can be detected in the multiphoton imaging mode.

The foregoing disclosed techniques and apparatus can be further employed to modify the refractive properties of ocular tissue (corneal stroma, crystalline lens) by creating (or machining) a GRIN structure within the ocular tissue. This is generally accomplished by continuously scanning a continuous stream of appropriate laser pulses having a controlled focal volume in and along at least one continuous line (scan line) in the tissue while varying the scan speed and/or the average laser power, which creates a smoothly changing refractive index in the tissue along the scan line. Accordingly, rather than creating discrete, individual, or even grouped or clustered, adjoining refractive index structures in the ocular tissue from one or more femtosecond laser pulses or bursts of pulses directed to a particular spot in the tissue, a smoothly changing gradient refractive index is created in the tissue by continuously scanning a continuous stream of pulses. As will be described in greater detail below, since the refractive modification in the tissue arises from a multiphoton absorption process, a well controlled focal volume corrected for spherical (and other) aberrations will produce a scan line having consistent and, if desired, constant depth over the length of the scan. As further noted, when a tightly focused laser beam consisting of femtosecond pulses at high repetition rate impinges on a sample that is nominally transparent at the incident laser wavelength, there is little if any effect on the material away from the focal region. In the focal region, however, the intensity can exceed one terawatt per square centimeter, and the possibility of absorbing two or more photons simultaneously can become significant. In particular, the amount of two photon absorption can be adjusted by doping the irradiated material with selected chromophores that exhibit large two-photon absorption cross-section at the proper wavelength, which can significantly increase the scanning speed. As further described below, multiple scan lines can be written into the tissue in a layer using different scan speeds and/or average laser power levels for different scan lines to create a gradient index profile across the layer (GRIN layer). Further, multiple, spaced GRIN layers can be written into the ocular tissue along the z-direction (i.e., generally the light propagation direction through the cornea or natural lens or other optic in or on the eye) to provide a desired refractive change in the eye that is corrected for some, most, or all higher order aberrations.

The discussion that follows will be described in terms of writing in a hydrogel material, but it is to be noted that the method and apparatus embodiments and aspects thereof described herein below are applicable to ocular tissue such as corneal stroma and the natural crystalline lens.

It is advantageous to calibrate the effect of scanning speed and laser power on the refractive index change. To do this, we wrote ten diffraction gratings at different writing speeds while keeping all other parameters constant and measuring the resulting diffraction efficiencies, thereby determining the index changes.

Figure 15:
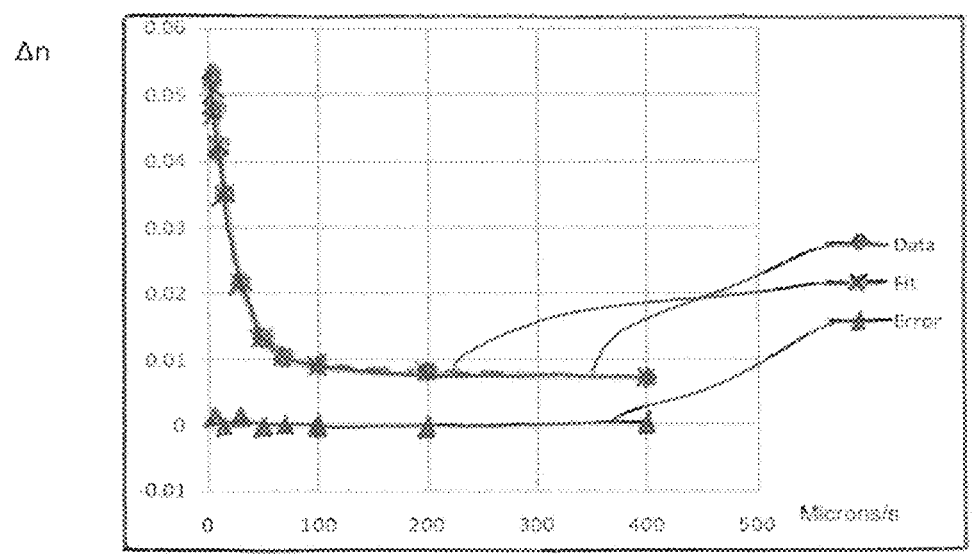
FIG. 15 is a graph showing index of refraction change (vertical axis) vs. scanning speed (horizontal axis in mm/sec) for Akreos hydrogel in BBS with 2% X-monomer doping at 370 mw average power at 800 nm with 100 fs laser pulses at 82 MHz repetition rate.

FIG. 15 shows the refractive index change in Akreos™ AO Lens (Bausch & Lomb) material as a function of the scanning speed in microns/sec for conditions of 400 mw average power, 100 fs pulse width, 800 nm wavelength and focusing using a 0.7 NA air immersion microscope objective. FIG. 15 also shows an empirical fit to the data. Using this empirical fit, we obtain the scan speed as a function of desired index change simply by inverting the relationship.

Using the calibration curve shown in FIG. 15, we can write 3D structures that have desired variable, or gradient, index of refraction simply by changing the scanning speed. Alternatively, or in combination with this, we can write 3D structures that have a desired gradient index by varying the laser (average) power.

Figure 16:
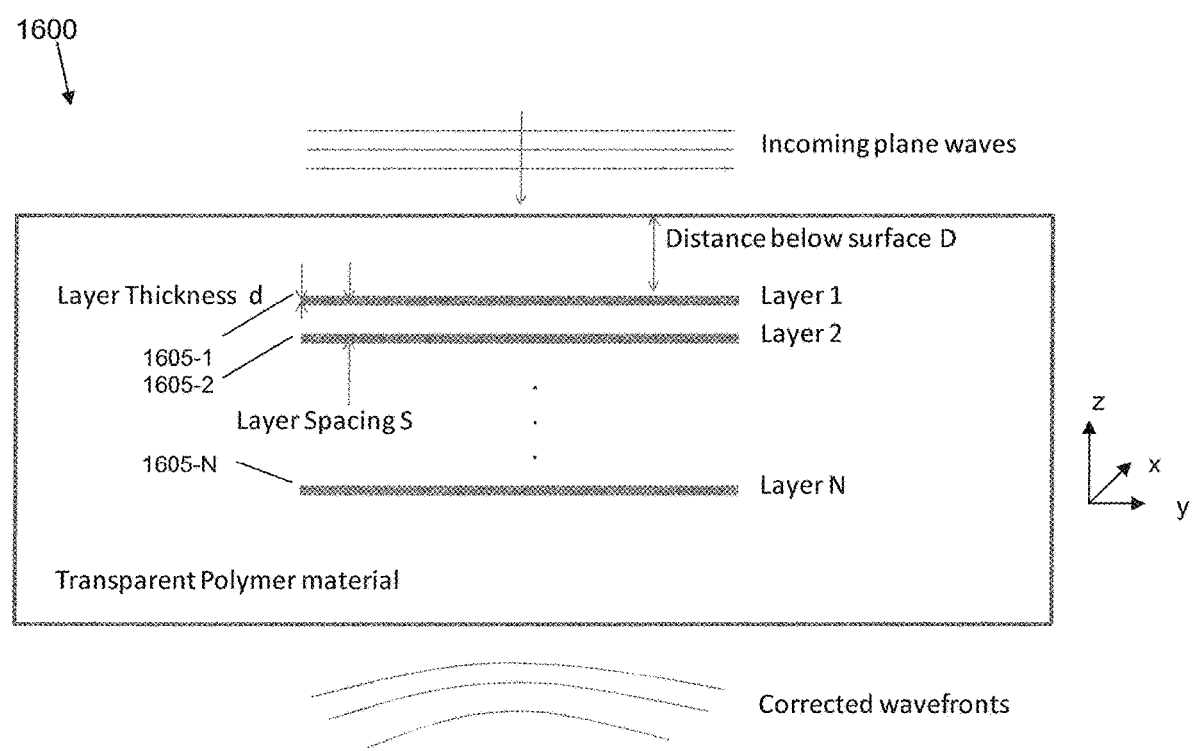
FIG. 16 shows a cross sectional schematic view of layered gradient index structures written into a flat plate of an ophthalmic hydrogel material.

For ophthalmic applications, it is of particular interest to write structures that have low scattering and high optical quality. FIG. 16 shows, in cross section, an ophthalmic hydrogel material 1600 in which lateral gradient index layers 1605-N of thickness, d (1-10 µm), extending into the paper (x-direction) having spacings, S, between the layers (z-direction) have been written (FIG. 16 could represent ocular tissue according to the embodied invention). As further described below and with reference to FIG. 17, each GRIN layer 1605 comprises a plurality N of straight scan lines 1701 that are substantially parallel and equally spaced, each scan line having a width of between about one to five µm (e.g., 2 µm) and an interline spacing that is equal to or less than the line width (e.g., line spacings may be 1 µm or less).

When writing gradient index microstructures in ophthalmic devices or ocular tissues, under some conditions the accumulated phase difference in some regions of the structure may exceed $2\pi$. In those regions, the design of the gradient index structure can be modified to provide a phase shift that is modulo-$2\pi$. In other words, in the regions where the phase shift is between $2\pi$ and $4\pi$, a constant phase shift of $2\pi$ can be subtracted from the total phase shift. Similarly, if the phase shift according to the design would place the phase shift in the range $4\pi$ to $6\pi$, then a constant $4\pi$ phase shift can be subtracted from the design in that region. This can be advantageous in some cases in helping to reduce the total device writing times.

In this kind of device design, the index of refraction varies within each layer in a prescribed manner according to the desired device functionality. For instance, if a focusing lens is desired, it will be advantageous to cause the index of refraction change to vary quadratically. If the maximum index change is in the center and the change decreases outward to the edges, then the structure will provide focusing power. In the reverse case, where the index change is maximum at the edges and decreases toward the center, such a structure will provide divergence, or negative focusing power. Furthermore, if one or more layers 1605 are written with a quadratic index change of a given magnitude and orientation (e.g., x-direction) and one or more different layers are written with a quadratic index change of different magnitude and orientation (e.g., y-direction), an astigmatic crossed-cylindrical lens structure results, which is applicable for vision correction in contact lenses, intra-ocular lenses, or in the human cornea or lens.

Figure 17:
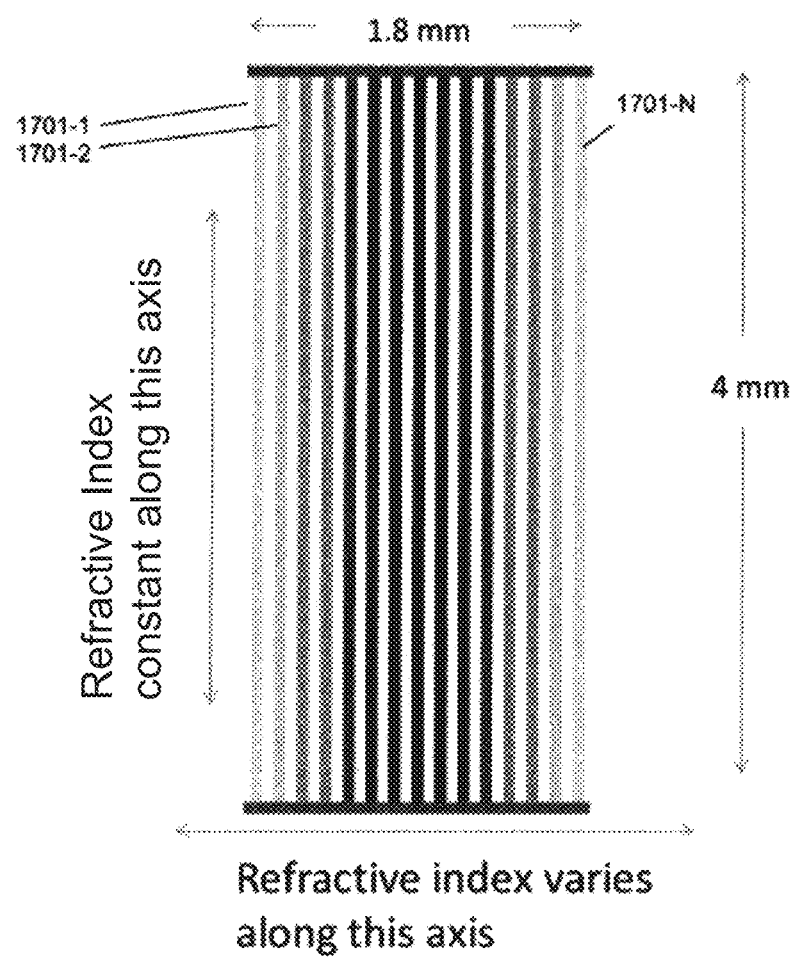
FIG. 17 shows a schematic view of multiple scan lines in a GRIN layer where each line is approximately two microns wide and the line spacing is one micron, according to an illustrative embodiment of the invention.

In an illustrative aspect, we wrote a cylindrical lens structure with a one-dimensional quadratic gradient index structure as shown in FIG. 16 with three GRIN layers each 5 µm thick as illustrated in FIG. 17, spaced by 10 µm (z-direction). The resulting cylindrical lens was designed to provide approximately 1 diopter of astigmatism uniform along the length of the device.

Figure 18A:
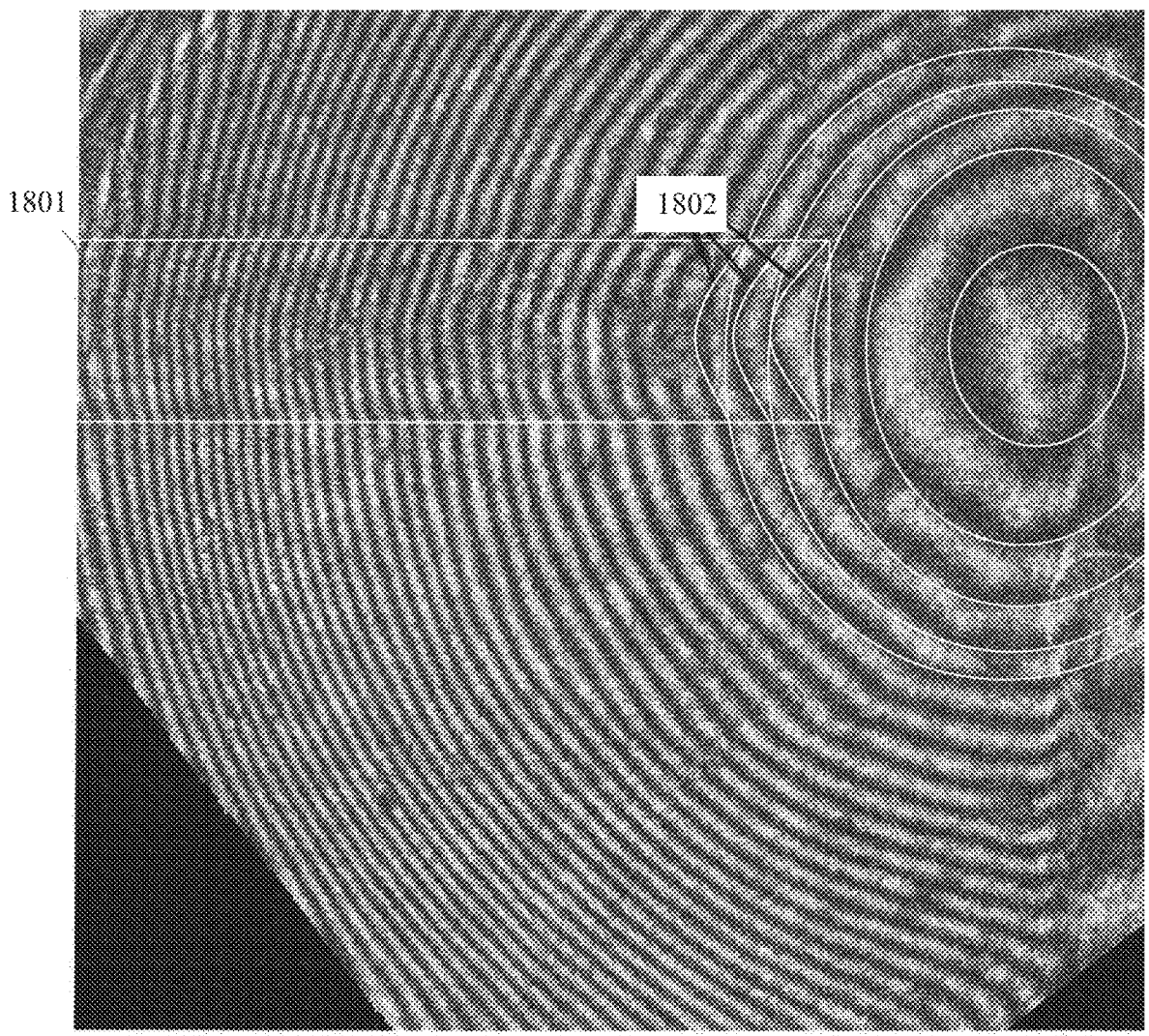
FIGS. 18A and 18B show a Twyman Green interferogram of a one dimensional quadratic gradient index device that is 1.8 mm wide by 4 mm long (rectangle) written in Akreos:X monomer (curved line segments show quadratic phasefronts), and a phase topography measurement that confirms the parabolic nature of the phase readings, according to an illustrative embodiment of the invention.
Figure 18B:
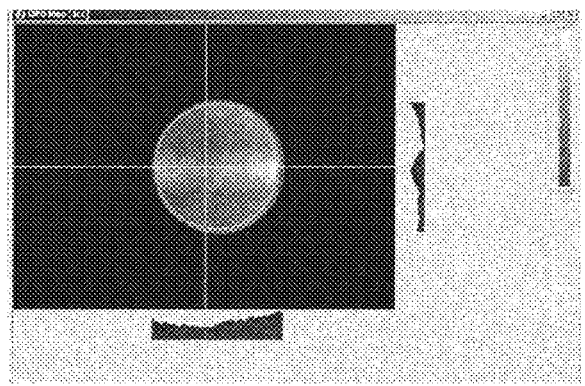

FIG. 18A shows a Twyman Green interferometer image of the lens structure 1801 (rectangular region) showing nominally quadratic phase contours 1802 (curved line segments) in the lens area. FIG. 18B shows a phase topography measurement that confirms the parabolic nature of the phase readings. Imperfections in the xyz high speed piezoelectric translation stage and scanning procedure cause localized index fluctuations that result in random phase shifts, but the general appearance of the fringes is as expected. The measured astigmatism (corrected for any baseline astigmatism in the glass and hydrogel substrate) varied between +0.3 and +0.9 diopters along the length of the sample. We speculate that this was caused by a nonuniformity in the scanning process, either in the scanning speed or in the line spacing. Furthermore, the 3D high speed ultrasonic piezoelectric stages that we used (PolyTek PI) exhibited some retracing errors wherein the return scan line was located a few microns below the height of the initially scanned line, which could have caused some random phase errors.

Such gradient index structures are highly versatile, and can be written, as described above, as vertically spaced (z-direction) layers with each layer being different in order to achieve different results. For hydrogel materials, e.g., in order to maintain high index change, it is advantageous to maintain a spacing between the layers in the range of 5 to 10 microns or so. Devices written with no spacing between the layers showed lower net index change. In order to keep the devices compact, it is desirable to minimize the spacing between the layers, e.g., 5-10 microns.

It is desirable to be able to correct not only sphere and cylinder in vision correction, but also higher-order aberrations. It is also desirable to provide advanced designs that can provide multi-focal effects in order to alleviate symptoms of presbyopia. Furthermore, it is desirable to minimize the effects of "rainbow," which is a diffraction-based effect, in which diffracted peaks are seen at angles $m\lambda=d \sin \theta$ where m is the diffraction order, $\lambda$ is the wavelength of interest, and d is the grating period. This effect is expected when the line spacing is larger than the wavelength of light being used for observation. We find that structures with 1 micron line spacing exhibit visible coloration effects, however reduction of the line spacing to 0.7 to 0.5 microns reduces the "rainbow" effect. In this process, it is important to minimize any material damage that can cause scattering, and this should be optimized as part of the device design, considering the specific requirements of the application.

In addition to the adaptive optics system and techniques described herein above, precise control of short light pulses from a laser to form a scan line(s) that can be written into eye tissue at a depth of up to five mm is herein disclosed. High (nearly diffraction-limited) focus is maintained by an adaptive optic element with real-time feedback during scanning operations using an active feedback that is provided by a two-photon fluorescence signal.

It is known that high numerical aperture (NA>0.7) microscope objectives effectively used for writing refractive index modifications in a polymer or ocular tissue have a maximum working depth of about 3.2 mm. It is further appreciated that the natural crystalline lens or an implanted IOL may be located at a depth of 5 mm or more behind the anterior corneal surface. Furthermore, aberrations induced at the corneal surface severely degrade the focused beam quality. The use of water immersion objectives provides increased focusing quality, but still with limited depth resolution. Use of water immersion generally requires applanation of the corneal surface during surgery. In addition, in order to write refractive corrections inside the IOL, it will be necessary to scan to regions of the cornea that are significantly off-axis, which will introduce large higher order aberrations and degrade the focused beam quality.

These recognized problems have encouraged a solution in the form of a method and apparatus that can achieve diffraction-limited focusing with air immersion using a long working distance (up to 12 mm), high NA (i.e., >0.5) objective integrated with a scanning system that provides real-time control of the focus and maintains it during the scanning process.

Figure 19:
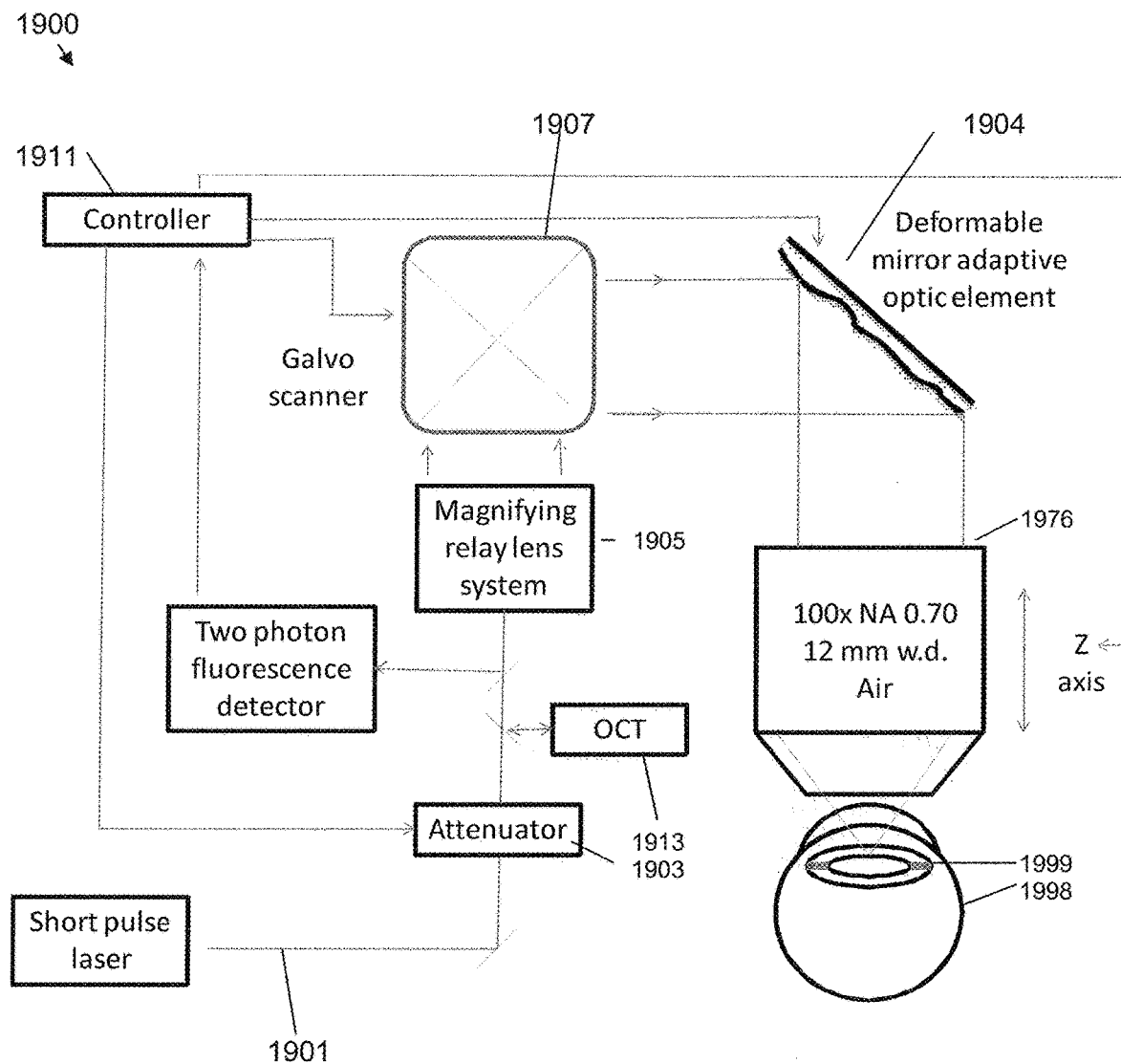
FIG. 19 shows a schematic view of an adaptive optic galvo-scanning system with real-time focusing feedback, according to an illustrative embodiment of the invention.

According to a non-limiting exemplary embodiment, an adaptive optic scanning system 1900 with real-time feedback is schematically illustrated in FIG. 19. A short pulse laser beam 1901 passes through a computer controlled beam attenuator 1903 to set the desired laser power. The beam then passes through a magnifying relay telescope 1905 that is designed to optimally fill the input pupil of a microscope objective 1976. The magnification and design of the relay lens system also is set to image a two dimensional galvanometer scanner 1907 into the input pupil of the microscope objective. The two-dimensional galvanometer scanner can provide high speed re-targeting of the beam typically in about 20 microseconds. After the galvanometer, the beam is reflected from a deformable mirror 1904. This is controlled by computer, and changes shape in response to signals from the computer and controller 1911. The light is focused into the eye 1998 and into the interior of an implanted IOL 1999 using a long working distance product inspection objective that has a 100×NA 0.70 specification with a working distance of 10-12 mm (such as Mitutoyo M PLAN NIR HR BF 100×NA 0.70, WD 10.0 mm or M PLAN NIR BF 100×NA 0.50, WD 12.0 mm). The Z-axis or focusing dimension is controlled with a Z-axis scanner (not shown) that is attached to the microscope objective, whereas the X-Y scanning will be provided by the galvanometer system. Additional scanning components may be included that provide scanning of the patient's head or, alternatively, scanning of the adaptive optic and focusing lens together.

The focusing performance of an NA 1.0 100X focusing objective that is designed for air immersion at a non-spherical interface consisting of layers of biological tissue produces a severely degraded focus. It is thus extremely advantageous to have a method of real-time feedback and a real-time compensation technique that provides instantaneous information regarding the quality of the focused beam, which must be maintained at near-diffraction-limited performance throughout the scanning operation.

According to an aspect, we use an epi-mode (back-detected), exogenous or endogenous (from a two-photon chromophore that is used as a two-photon enhancer in the IOL or ocular tissue) two-photon fluorescence signal as a detector of the focus quality.

For example, we first do a wavefront aberration test on the patient to determine the required corrections that are to be written into the IOL or ocular tissue. Next, once the patient is in place, a preliminary scan is done with the OCT (optical coherence tomography) system 1913 to locate the interfaces of the IOL or tissue. Then the laser is run at low power (~5 mw) and the two photon fluorescence signals are detected. The two photon fluorescence signal at each of a defined grid of points is optimized such that the two-photon signal is optimized at each scan point in the aberration correction grid. At each point, then, the optimum settings of the deformable mirror can be determined that give the highest two-photon fluorescence signal. The settings are then saved for the scanning process. When the scan pattern is to be written, the laser is turned up to high power, and the scanning commences. At each galvo-scanning point, the deformable mirror returns to the wavefront correction setting that provided the optimum focusing and the highest two-photon fluorescence signal, thereby providing nearly diffraction-limited focusing throughout the scan region.

The aberration correction grid does not have to be as fine as the micromachining grid, but should be fine enough so that the aberrations are corrected on a fine enough scale so that the focusing is maintained at nearly diffraction-limit throughout the scanning process. An interpolation routine may be developed so that a rough correction grid could be taken, and then the aberration correction could simply be interpolated inside the grid points for higher efficiency.

It will be appreciated that the magnitude of the endogenous or intrinsic multiphoton fluorescence, which may be obtained with shorter wavelength (e.g., blue) excitation light may or may not be sufficient for the real-time feedback described above. A two-photon fluorescence enhancer may be used to create exogenous multiphoton fluorescence from the ocular tissue. Furthermore, it may be necessary to include a separate aberration compensator for scanning at maximum depths (greater than 3 mm.) to offset larger amounts of aberration than can be compensated by the adaptive optical element.

Figure 20A:
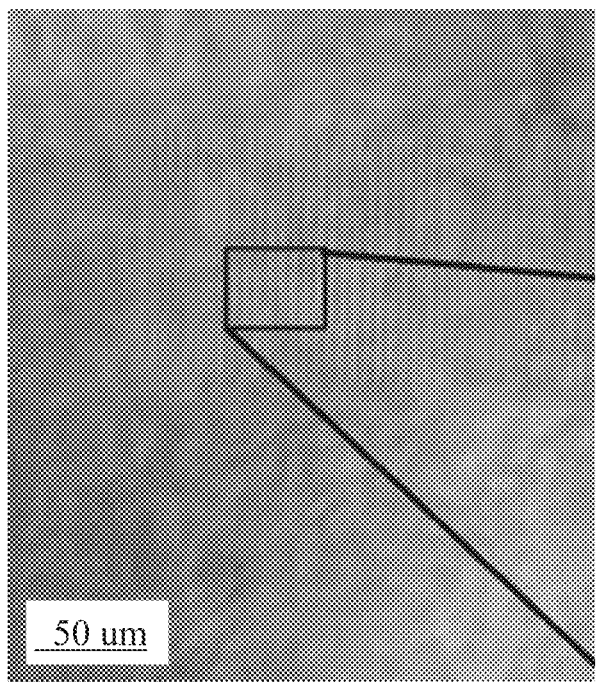
FIGS. 20A and 20B show a Differential Interference Contrast (DIC mode) photo of NIR femtosecond IRIS in lightly-fixed post-mortem corneal tissue. Refractive index change of 0.008 was obtained at a scanning speed of 0.7 µm/s, with a pulse energy of 0.3 nJ, according to an illustrative aspect of the invention.
Figure 20B:
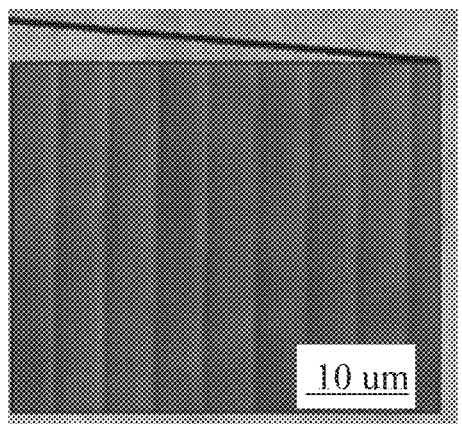

Previously, the initial IRIS (Intra-tissue Refractive Index Shaping) was done in lightly-fixed post-mortem cat cornea using a low-pulse-energy femtosecond laser at 800 nm. FIGS. 20A and 20B show the DIC image of periodic grating lines created by NIR femtosecond IRIS (NIR-IRIS). Low-scattering-loss refractive index (RI) changes along the grating line were obtained and averaged ~0.008. However, these changes were only achievable at an extremely slow scanning speed of 0.7 μm/s.

Figure 21:
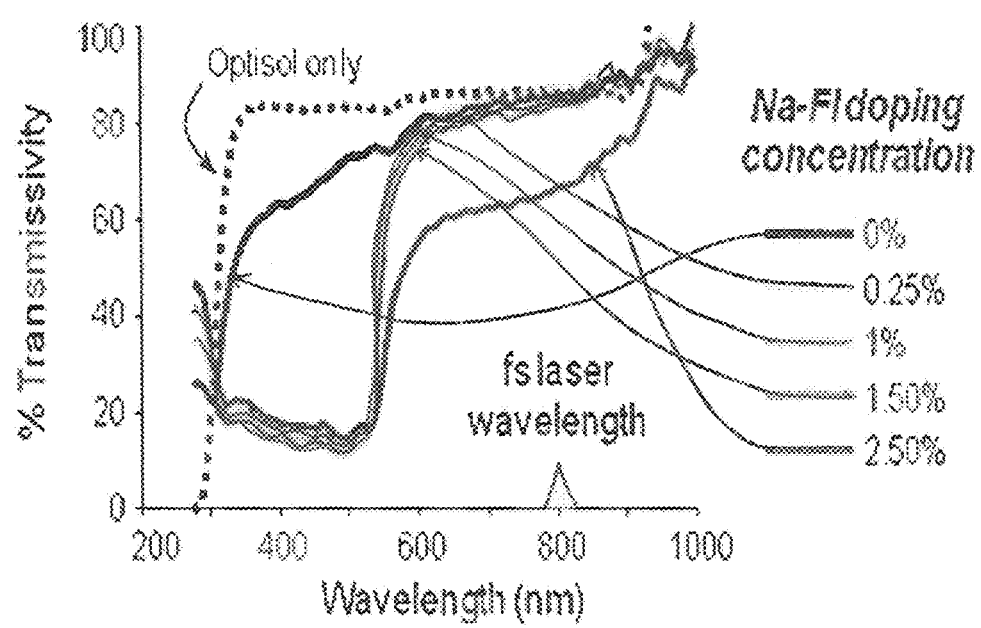
FIG. 21 is a graph that shows the effect of sodium fluorescein doping (0%, 0.25%, 1%, 1.50%, 2.50%) on the transmission spectrum of living corneal tissue, which is stored in Optisol-GS solution, according to an illustrative aspect of the invention.

We measured the transmission spectrum of living corneal tissue both undoped and doped with sodium fluorescein (Na-Fl), which is commonly used in ophthalmic practice. The spectrum shown in FIG. 21 shows that using NIR femtosecond laser pulses at 800 nm, there is almost no direct one-photon absorption and very weak two photon absorption (TPA) when the cornea is undoped. When Na-Fl is doped into the cornea, the TPA of the corneal tissue is largely enhanced, due to an absorption window from ~300 to ~500 nm. Thus, greater RI changes are expected at much faster scanning speeds.

Figure 22:
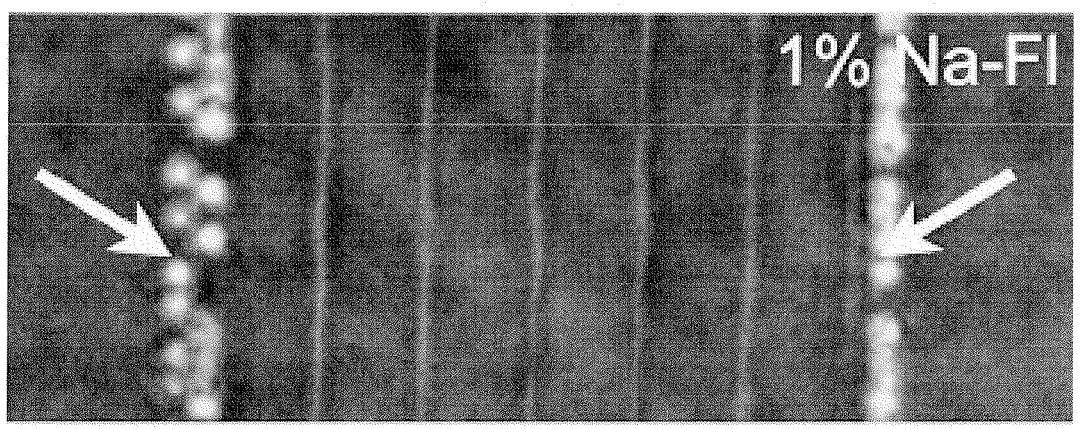
FIG. 22 shows near infra-red (NIR) femtosecond IRIS in living corneal tissue doped with 1% Na-Fl (scanning speed is 2 mm/s and pulse energy is ~1.5 nJ; refractive index change ~0.012, according to an illustrative aspect of the invention.

FIG. 22 gives one example of NIR-IRIS in living corneal tissue doped with 1% Na-Fl, where RI change of ~0.012 was attained at a scanning speed of 2 mm/s. A range of scanning speeds and Na-Fl doping concentrations were tested, and the results are plotted in FIG. 5 (NIR-IRIS with Na-Fl doping) [4]. Thus, NIR-IRIS could be largely enhanced by doping exogenous substances as TPA sensitizer.

Figure 23:
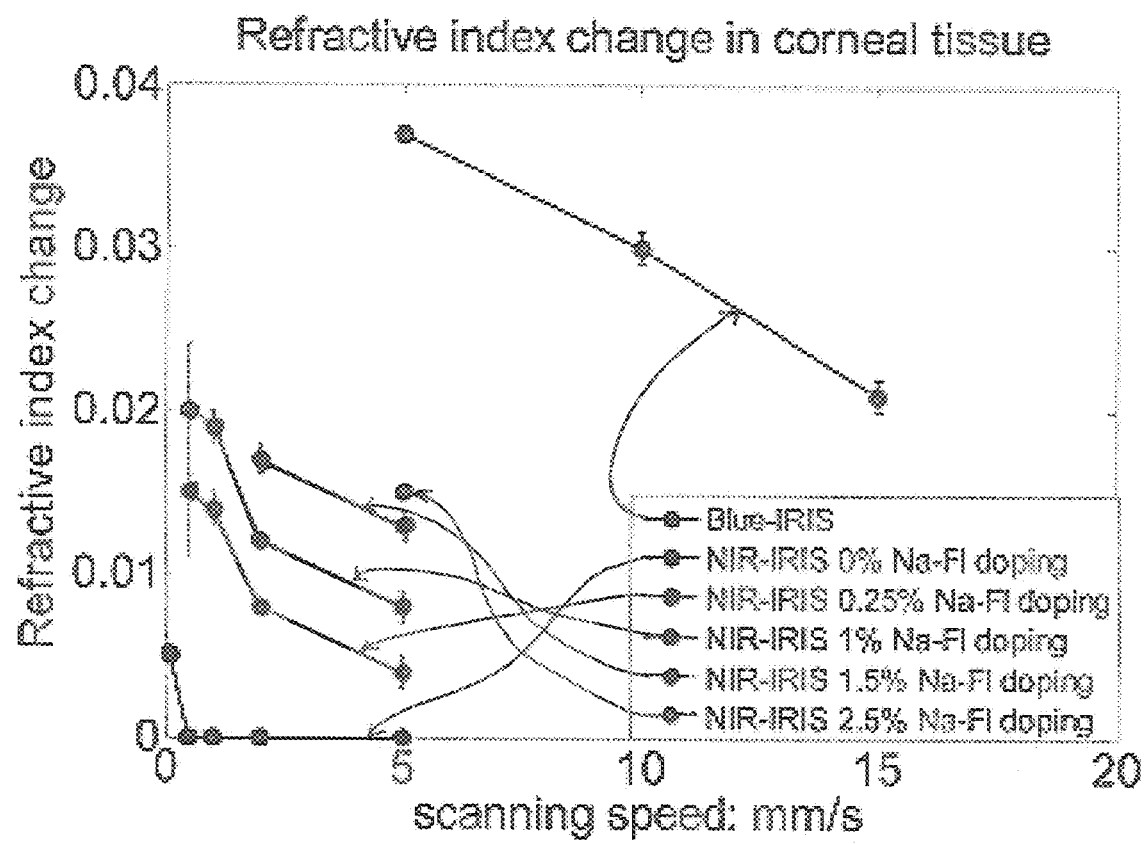
FIG. 23 graphically shows refractive index change in live cornea induced by Blue-IRIS in undoped corneal tissue and NIR-IRIS in corneal tissue doped with various concentrations of sodium fluorescein, according to an illustrative aspect of the invention.

NIR-IRIS in living cornea doped with Na-Fl doping induces greater RI change at much faster scanning speeds as compared to IRIS in fixed cornea; however, it relies on exogenous doping to increase the effectiveness. The corneal epithelium layer acts like a barrier and needed to be scrapped off to allow Na-Fl to penetrate into the corneal stroma. Epithelial removal creates a surface wound and a wound healing response in the cornea, which disrupts optical quality and creates a significant complication for both live animal studies and human applications. Above, we described a process referred to as "Blue" intratissue refractive index shaping (Blue-IRIS) using femtosecond laser pulses at 400 nm. Without the need for epithelial removal or TPA enhancement, Blue-IRIS achieves even better optical results in native, live corneas (see FIG. 14, showing a periodic grating inscribed in undoped live cornea by Blue-IRIS. A RI change of ~0.037 was obtained at a scanning speed of 5 mm/s). As shown in FIG. 23, a scanning speed up to 15 mm/s still induced a RI change of 0.021. In the case of NIR-IRIS with Na-Fl doping, a maximum RI change of 0.02 was obtained at a scanning speed of 0.5 mm/s. Thus, a similar RI change can be induced with Blue-IRIS at scanning speed that is 30× faster than that of NIR-IRIS. The maximum achievable RI change is also largely increased. We believe that the large enhancement of Blue-IRIS is attributed to stronger TPA of the cornea when using blue femtosecond laser pulses at 400 nm, given that the cornea has strongest absorption in the ultraviolet regime. Hence, endogenous two photon absorption is even more efficient for IRIS, without the need of doping exogenous two-photon enhancer, which creates significant complications for clinical studies.

The results of IRIS with exogenous and endogenous two-photon absorption enhancement are plotted in FIG. 23. Compared to IRIS in fixed cornea where RI change was only 0.008 at 0.7 µm/s, these two methods have shown a significant improvement of the femtosecond IRIS procedure in terms of both attainable RI change and scanning speed. Exogenous doping of Na-Fl indeed increases the effectiveness of NIR-IRIS, but suffers from complications immediately following corneal epithelium removal, which is necessary for Na-Fl to penetrate through the stroma. Blue-IRIS utilizes the endogenous two-photon enhancement when femtosecond laser pulses at 400 nm are used. Attainable RI change and scanning speeds are further improved without the need for doping exogenous substances or disruption of the corneal epithelium, which makes it the most minimally invasive among all current refractive surgical procedures, including IRIS, LASIK, PRK, etc.

As mentioned above, the disclosed gradient index structure can be effectively written directly into the human (or animal) cornea or crystalline lens by a similar process, provided care is take to compensate for the optical aberrations that result when writing deep into such material. The use of a NA 0.7 microscope objective provided optimum results in terms of dynamic range (the range of index of refraction changes that can be obtained above baseline and before damage sets in). At such a high NA, it is necessary to fully compensate the relevant aberrations, most importantly spherical aberration.

Discussion of GRIN Layers

Figure 24:
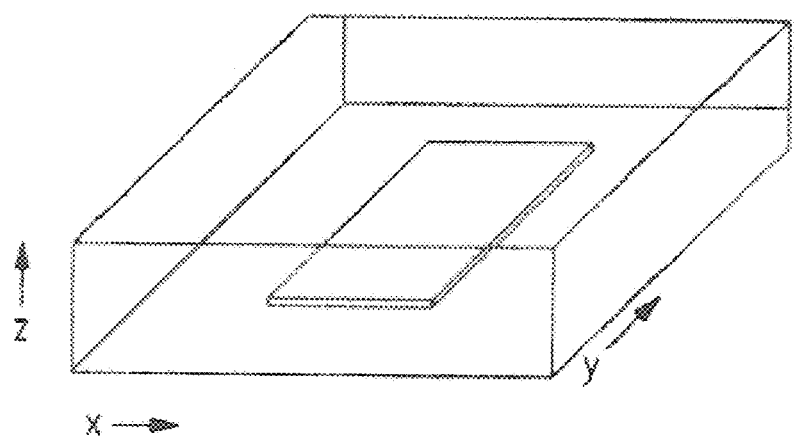
FIG. 24 shows a schematic view of a single gradient index layer written in a flat material, according to an illustrative aspect of the invention.

An xyz translation system can be used to write gradient index layers. The thin (1-10 µm) layers cause a variable phase shift in the plane, resulting in a curvature of the phase fronts of the light. FIG. 24 shows a three-dimensional representation of a single, thin GRIN layer written into a flat piece of polymer material. There are several modes in which refractive devices can be written. Since the index of refraction change depends on the scan speed as well as the optical power, we can write refractive devices using either mode, or both together. We refer to these herein as "speed mode" and "power mode" for convenience.

1) In 1D Speed Mode, to write a single, thin GRIN layer, the translator is first set to the required z-position to set the height of the layer inside the material. Then, the translator is scanned along the y-direction at a speed that is uniform along y, but different for each x value. For instance, the speeds can be programmed to produce a parabolic index change. This will produce a cylindrical lens with refracting power in the x-direction that is uniform in the y-direction. In 2D Speed Mode, the translator is scanned along the y-direction at a non-uniform speed such that the index change is non-uniform along the y-direction. The non-uniform y-speed can also be changed along the x-direction, resulting in a two-dimensional gradient index layer.

2) In 1D Power mode, to write a single, thin GRIN layer, the translator is first set to the required z-position to set the height of the layer inside the material. Then, the translator is scanned along the y-direction at a uniform speed and the intensity of the femtosecond laser pulses is set to a different average power by a light modulator such as an acousto-optic or electro-optic modulator for each y-scan. As a result, the index change is different for each x-position. For instance, the intensities may be set to produce a quadratic index variation along the x-direction. In 2D Power Mode, the light intensity is varied continuously along the y-scan during the y-scan, and the light intensities can varied for each x-position. This results in a two-dimensional gradient index layer.

Figure 25:
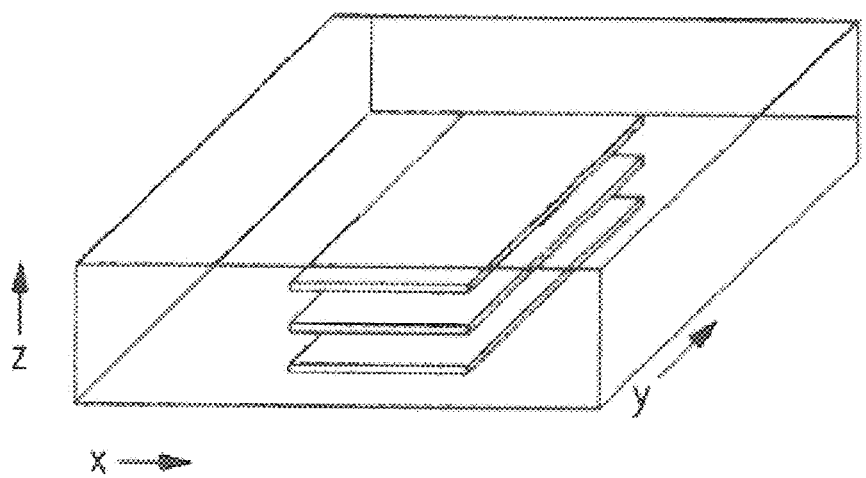
FIG. 25 shows a schematic view of a three layer gradient index pattern written in a flat sample, according to an illustrative aspect of the invention.

Either of these techniques can be repeated, and after each layer is written, the z-axis is translated such that the layers are separate by 5-10 microns. FIG. 25 shows the result as three layers are written. Each layer may have different gradient index properties, or they could be the same. For instance, one layer may have the index gradient in the x-direction and another layer may have the index gradient in the y-direction. This would result in a "crossed cylinder" optical approach. which is similar to a spherical lens, except that it offer certain design degrees of freedom.

3) Combined Speed and Power mode. In some cases, it may be advantageous to combine these modes. For instance, Power Mode could be used to vary the index change along the y-direction, and the scan speeds could be varied along the x-direction, and/or the reverse.

Figure 26:
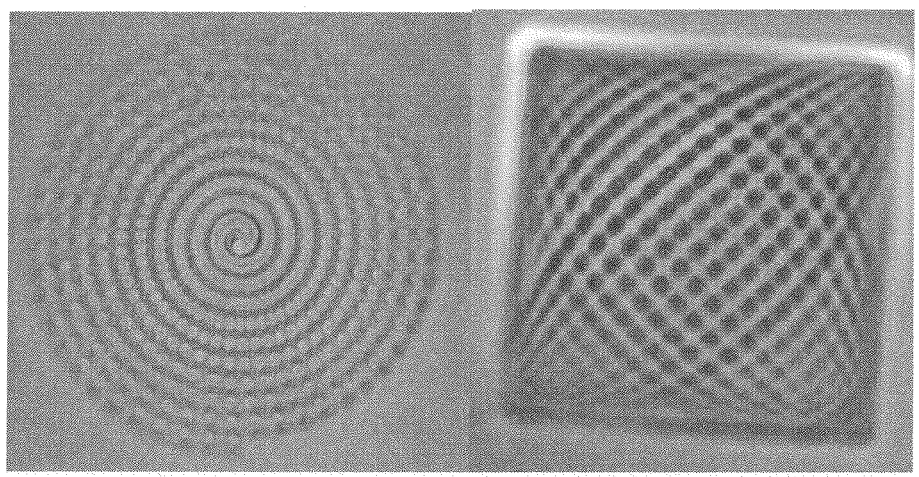
FIG. 26 shows two-dimensional, single-layer gradient index devices written in Thiol-ene:ITX with a galvo controlled system, according to an illustrative aspect of the invention.

4) Galvanometer controlled systems. In the case of scanning systems that use galvanometer-type of control systems, it is possible to address different points in the sample at high speeds in arbitrary patterns, resulting in complex gradient index possibilities. In this case, the localized index changes will depend on the laser power modulation and the local scanning speed. Using a two dimensional galvo system with a custom designed optical relay lens system, we wrote two dimensional gradient index structures in Thiol-ene doped with ITX. FIG. 26 shows some preliminary results obtained by driving the galvanometers in out-of phase repetitive patterns. These are commonly referred to as Lissajous patterns. It is possible to write two-dimensional gradient index patterns with radially symmetric index gradient using such a system, and the control system for such a writing procedure could use a combination of scan speed control and optical power control as discussed previously for the case of xyz scanning.

Typically, galvo-controlled systems designed for high NA focusing are limited to scanning over a small area (e.g., 350-450 µm diameter) as a result of their short effective focal length. In order to write larger devices, it will be necessary to design a high NA large field optical system, or to stack the scanning systems and use a combination of galvo-scanning and sample translation, for example. Planar gradient index structures such as those shown in FIG. 26 can be written in multiple layers also as shown in FIG. 25, and again, the gradient index designs of each layer could be the same, or they could be different.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening.

The recitation of ranges of values herein are merely intended to serve as a shorthand method of referring individually to each separate value falling within the range, unless otherwise indicated herein, and each separate value is incorporated into the specification as if it were individually recited herein.

All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not impose a limitation on the scope of the invention unless otherwise claimed.

No language in the specification should be construed as indicating any non-claimed element as essential to the practice of the invention.

It will be apparent to those skilled in the art that various modifications and variations can be made to the present invention without departing from the spirit and scope of the invention. There is no intention to limit the invention to the specific form or forms disclosed, but on the contrary, the intention is to cover all modifications, alternative constructions, and equivalents falling within the spirit and scope of the invention, as defined in the appended claims. Thus, it is intended that the present invention cover the modifications and variations of this invention provided they come within the scope of the appended claims and their equivalents.

We claim:

1. A method for modifying a refractive property of ocular tissue in an eye, comprising:
   determining a desired vision correction adjustment;
   determining a position, number, and design parameters of one or more optically modified gradient index (GRIN) layers to be created within the ocular tissue to provide the desired vision correction;
   writing the one or more determined GRIN layers by creating at least one GRIN layer in at least one of the corneal stroma and the crystalline lens having a gradient index of refraction in the at least one GRIN layer in two orthogonal directions that are generally transverse to a direction of light propagation through the ocular tissue by scanning a stream of laser pulses having a focal volume from a laser having a known average power along a line having a smoothly changing refractive index within the tissue; and
   varying one or more laser parameter including at least one of scan speed, laser average power, wavelength, and pulse width during the scan; and determining the varied one or more laser parameter as a function of a selected gradient index of refraction along a scan line.

2. The method of claim 1, further comprising continuously scanning a continuous stream of laser pulses having a constant focal volume.

3. The method of claim 1, wherein the one or more determined GRIN layers each have a GRIN layer thickness of at least one µm.

4. The method of claim 1, further comprising creating a plurality of laser scan lines in an adjacent, spaced relationship in the ocular tissue.

5. The method of claim 4, further comprising creating a plurality of straight scan lines.

6. The method of claim 5, wherein each of the lines has a width of at most five µm and an interline spacing that is equal to or less than the line width.

7. The method of claim 5, wherein each of two adjacent lines has a width of at most five µm and an interline spacing that is equal to or less than an average of the two adjacent line widths.

8. The method of claim 6 wherein the spacing is less than one µm.

9. The method of claim 1, wherein the GRIN layer is a planar layer.

10. The method of claim 1, further comprising determining the scan speed as a function of the selected gradient index of refraction along the scan line.

11. The method of claim 1, further comprising scanning with a laser beam having a wavelength in the range from 650 nm to 1000 nm, an average laser power from 50 mW to 1000 mW, a pulse width of between 5 fs to 200 fs, a pulse repetition rate of between 10 MHz to 500 MHz, and a pulse energy between 0.01 nJ and 100 nJ, and providing a two-photon sensitizer in the ocular tissue.

12. The method of claim 1, further comprising scanning with a laser beam having a wavelength in the range from 350 nm to 600 nm, an average laser power from 20 mW to 400 mW, a pulse width of between 30 fs to 200 fs, a pulse repetition rate of between 10 MHz to 500 MHz, and a pulse energy between 0.1 nJ and 20 nJ.

13. The method of claim 1, further comprising creating at least one of a quadratic and a non-quadratic gradient index profile in the GRIN layer.

14. The method of claim 1, further comprising:
   determining the corrected vision after writing the one or more determined GRIN layers.

15. The method of claim 1, wherein the refractive property of ocular tissue in an eye is modified to form a refractive structure having a structural form of at least one of a lens, a prism, a Bragg grating, a microlens arrays, a zone plate, a Fresnel lenses, and a combination thereof.

16. The method of claim 1, wherein the refractive property of ocular tissue in an eye is modified to provide astigmatism correction.

17. The method of claim 1, wherein the laser pulses having a focal region in the form of a cylindrical volume from about 0.5 µm to 3 µm in diameter and 3 µm to 10 µm in length.

18. A method for modifying a refractive property of ocular tissue in an eye, comprising:
   determining a desired vision correction adjustment;
   determining a position, number, and design parameters of one or more optically modified gradient index (GRIN) layers to be created within the ocular tissue to provide the desired vision correction;
   writing the one or more determined GRIN layers by creating at least one GRIN layer in at least one of the corneal stroma and the crystalline lens having a gradient index of refraction in at least two directions that are generally transverse to a direction of light propagation through the ocular tissue by scanning a stream of laser pulses having a focal volume from a laser having a known average power along a line having a smoothly changing refractive index within the tissue; and
   varying one or more laser parameter including at least one of scan speed, laser average power, wavelength, and pulse width during the scan; and determining the varied one or more laser parameter as a function of a selected gradient index of refraction along a scan line; and
   further comprising creating at least two optically-modified GRIN layers having an interlayer spacing, S, equal to or greater than five µm.

19. The method of claim 18, further comprising creating a quadratic gradient index of refraction of one given magnitude and orientation in the at least one GRIN layer and a quadratic gradient index of refraction of a different given magnitude and orientation in the at least another GRIN layer.

20. The method of claim 19, further comprising creating a cylindrical focusing power in the ocular tissue.

* * * * *